United States Patent
Leube et al.

(10) Patent No.: US 11,445,904 B2
(45) Date of Patent: Sep. 20, 2022

(54) JOINT DETERMINATION OF ACCOMMODATION AND VERGENCE

(71) Applicant: Carl Zeiss Vision International GmbH, Aalen (DE)

(72) Inventors: Alexander Leube, Aalen (DE); Arne Ohlendorf, Tübingen (DE); Siegfried Wahl, Donzdorf (DE)

(73) Assignee: Carl Zeiss Vision International GmbH, Aalen (DE)

(*) Notice: Subject to any disclaimer, the term of this patent is extended or adjusted under 35 U.S.C. 154(b) by 0 days.

(21) Appl. No.: 17/590,247

(22) Filed: Feb. 1, 2022

(65) Prior Publication Data

US 2022/0151484 A1 May 19, 2022

Related U.S. Application Data

(63) Continuation of application No. PCT/EP2020/073494, filed on Aug. 21, 2020.

(51) Int. Cl.
*A61B 3/032* (2006.01)
*A61B 3/09* (2006.01)
(Continued)

(52) U.S. Cl.
CPC ............... *A61B 3/032* (2013.01); *A61B 3/09* (2013.01); *A61B 3/103* (2013.01); *A61B 3/113* (2013.01); *A61B 3/18* (2013.01)

(58) Field of Classification Search
CPC .......... A61B 3/032; A61B 3/09; A61B 3/103; A61B 3/113; A61B 3/18; A61B 3/028; A61B 3/0025; A61B 3/0041
(Continued)

(56) References Cited

U.S. PATENT DOCUMENTS

| 5,684,561 A | 11/1997 | Yancey |
| 6,402,320 B1 | 6/2002 | Borchert |

(Continued)

FOREIGN PATENT DOCUMENTS

| DE | 102012022662 A1 | 5/2014 |
| EP | 3730037 A1 | 10/2020 |

(Continued)

OTHER PUBLICATIONS

International Search Report issued in PCT/EP2020/073494, to which this application claims priority, completed Aug. 4, 2021, and English-language translation thereof.

(Continued)

*Primary Examiner* — Mohammed A Hasan
(74) *Attorney, Agent, or Firm* — Tautz & Schuhmacher LLC; Georg Hasselmann

(57) ABSTRACT

Methods and apparatuses for joint determination of accommodation and vergence of at least one eye of a user are disclosed. The joint determination includes determining an accommodation of the eye of the user and ascertaining values for checking myopia of the eye by presenting a sign at a first distance in front of the eye to stimulate the accommodation of the eye; capturing an eye movement; ascertaining a refraction of the eye with the accommodation of the eye at the first distance; and joint determination of accommodation and vergence of the eye by ascertaining a change in the refraction of the eye with the accommodation of the eye at the first distance in relation to the accommodation of the eye at a second distance; and ascertaining the vergence of the eye from the eye movement of the eye with the accommodation of the eye at the first distance.

22 Claims, 2 Drawing Sheets

(51) Int. Cl.
    *A61B 3/103*    (2006.01)
    *A61B 3/113*    (2006.01)
    *A61B 3/18*     (2006.01)
(58) Field of Classification Search
    USPC .......................................................... 351/209
    See application file for complete search history.

(56) References Cited

U.S. PATENT DOCUMENTS

| | | | |
|---|---|---|---|
| 7,290,879 | B2 | 11/2007 | Nagata et al. |
| 8,506,084 | B2 | 8/2013 | Esser et al. |
| 9,572,486 | B2 | 2/2017 | Voigtmann et al. |
| 2009/0153796 | A1* | 6/2009 | Rabner .................. A61B 3/024 351/203 |
| 2012/0287398 | A1 | 11/2012 | Baker et al. |
| 2013/0176534 | A1 | 7/2013 | Frankfort et al. |
| 2015/0070273 | A1 | 3/2015 | He et al. |
| 2016/0270656 | A1* | 9/2016 | Samec ............... G02B 27/0179 |
| 2018/0136486 | A1* | 5/2018 | Macnamara ............ G06F 3/013 |

FOREIGN PATENT DOCUMENTS

| | | |
|---|---|---|
| EP | 3756534 A1 | 12/2020 |
| WO | 200907136 A1 | 1/2009 |

OTHER PUBLICATIONS

Gwiazda et al. "Myopic Children Show Insufficient Accommodative Response to Blur," Investigative Ophthalmology & Visual Science 34(3), pp. 690 to 694, 1993.

Blignaut et al. "Mapping the Pupil-Glint Vector to Gaze Coordinates in a Simple Video-Based Eye Tracker," Journal of Eye Movement Research 7(1):4, pp. 1 to 11, 1995.

Thibos et al. "Power Vectors: An Application of Fourier Analysis to the Description and Statistical Analysis of Refractive Error," Optometry and Vision Science 74 (6), pp. 367 to 375, 1997.

Gwiazda et al "Response AC/A ratios are elevated in myopic children," Ophthalmic and Physiological Optics, vol. 19, No. 2, pp. 173 to 179, Mar. 1, 1999.

Gwiazda et al. "Accommodation, Accommodative Convergence, and Response AC/A Ratios Before and at the Onset of Myopia in Children," Optometry and Vision Science 82(4), pp. 273 to 278, 2005.

Win-Hall et al. "Objective accommodation measurements in prepresbyopic eyes using an autorefractor and an aberrometer," J. Cataract. Refract. Surg. 34(5), pp. 774 to 784, 2008.

Industrial Norm "Ophthalmic optics—Spectacle lenses— Vocabulary (ISO 13666:2012)," German and English version EN ISO 13666:2012, Oct. 2013.

Leube et al. "Individual neural transfer function affects the prediction of subjective depth of focus," Scientific Reports 8(1), 1919, 2018.

Written Opinion issued in PCT/EP2020/073494, to which this application claims priority, dated Jan. 15, 2021.

International Search Report issued in PCT/EP2020/073494, to which this application claims priority, dated Jan. 15, 2021, and English-language translation thereof.

* cited by examiner

JOINT DETERMINATION OF ACCOMMODATION AND VERGENCE

CROSS REFERENCE TO RELATED APPLICATIONS

This application is a continuation application of international patent application PCT/EP2020/073494, filed Aug. 21, 2020, designating the United States and claiming priority from European application 19193432.2, filed Aug. 23, 2019, and the entire content of both applications is incorporated herein by reference.

TECHNICAL FIELD

The present disclosure relates to methods and apparatuses for jointly determining accommodation and vergence of at least one eye of a user, for determining an accommodation of at least one eye of a user, for determining values for a control of myopia of at least one eye of the user, and for producing a spectacle lens for the user, data processing apparatuses, and associated computer programs, computer-readable data media, data medium signals and computer-readable media. Consequently, the present disclosure can be used for the control of myopia in particular; however, further fields of use are conceivable.

BACKGROUND

The related art has disclosed methods and apparatuses for determining accommodation and vergence of one eye or both eyes of a user, in particular for the control of myopia. However, the control of myopia is usually carried out in a standardized way without an influence of individual physiological parameters being taken into account in the process. In clinical applications, standard addition values and/or inset values are used for, e.g., progressive addition lenses which assist a near setting of the eye and thus are intended to slow the advance of nearsightedness (myopia), but individually measured parameters in relation to accommodation and/or vergence are not considered. In the current clinical routine, information about the accuracy of the accommodation and a near setting of the eyes arising therefrom is obtained by subjective and/or objective processes. Such processes, for example measuring a near malposition of the eyes by way of auxiliary prisms, however require trained staff and a subjective estimate, in particular in relation to blur or setting movements of the eyes. Apparatuses and methods known from the related art determine the accommodation and the vergence of the eyes of a user separately in each case, with the additional assumption being made that the outlay of each eye for accommodation corresponds to exactly one stimulus value.

However, the accommodation and the vergence of the eyes of a user cannot be considered completely independently of one another. In measurements regarding the accuracy of the accommodation of the eye, it was possible to demonstrate that a reduction in an accommodation error by way of progressive addition lenses depends significantly on a chosen addition power. Gwiazda J., Thorn F., Bauer J. and Held R., *Myopic Children Show Insufficient Accommodative Response to Blur*, Investigative Ophthalmology & Visual Science 34(3), 1993, pp. 690-94 could demonstrate that an inaccuracy of the accommodation of myopic subjects exceeds that of non-myopic subjects. Furthermore, according to Gwiazda J., Thorn F., and Held R., *Accommodation, Accommodative Convergence, and Response AC/A Ratios Before and at the Onset of Myopia in Children*, Optometry and Vision Science 82(4), 2005, pp. 273-78, the absolute value of the vergence set for a certain accommodation distance (abbreviated "AC/A" from accommodative convergence accommodation) is greater than the actually required absolute value in the case of myopic persons, and so the resultant aberration is greater than in the case of non-myopic subjects.

Win-Hall D. M., and Glasser, A., *Objective accommodation measurements in prepresbyopic eyes using an autorefractor and an aberrometer*, J. Cataract. Refract. Surg. 34(5), 2008, pp. 774-84, conducted a study for determining the repeatability of determination of the accommodation by means of an aberrometer and in an autorefractor in young and phakic prepresbyopic subjects. The accommodation was excited by means of symbols at different distances. The study yielded that the accommodation determined in both ways exhibited no significant differences and therefore is suitable for objectively determining the accommodation in a phakic prepresbyopic population with low accommodative amplitudes.

U.S. Pat. No. 5,684,561 A discloses an autorefractor comprising two light sources and an associated optical unit for projecting an image onto the eye fundus, wherein a single detector generates a signal that corresponds to each light source. A single light source and two detectors are used in an alternative configuration. The light reflected by the eye fundus is detected and differences between the two signals are used to determine deviations from a zero diopter sphere. Segmented or CCD detectors are used to determine cylinder, axis, length and line of sight, and to determine and analyze a retinal image therefrom.

U.S. Pat. No. 7,290,879 B2 discloses a combined apparatus for determining the refraction and accommodation function of the eye. The apparatus for determining the refraction comprises a switching device which facilitates a choice between two different types of measurement, comprising a normal measurement of the refraction, which captures the spherical refraction, the cylindrical refraction and the astigmatic axis, and a measurement of the accommodation function, which captures a change in the refraction of the eye for high-frequency components.

U.S. 2012/0287398 A1 discloses a binocular viewing analysis apparatus for determining a prescription of ocular aids for the eyes of a user. The apparatus comprises an optical system configured to represent virtual images for a target visible to one of the two eyes in each case. At least one beam splitter, arranged in front of each of the two eyes, guides the virtual images to the corresponding eyes. The apparatus further comprises devices for the spherical correction and for the cylindrical correction, which are respectively assigned to one of the two eyes and from which the respective refraction of the eye is determinable. An optional device for determining pursuit eye movements can be used to record the eye positions and adapt the position of the optical system therefrom.

Furthermore, methods and apparatuses for determining eye movements of a user are known.

U.S. Pat. No. 6,402,320 B1 discloses an automated method for determining a visual acuity, in particular for infants, by means of an electronic visual display device, said method comprising the following steps: (a) providing a fixation target on the display device as a stimulus for the user; then (b) providing a test image on the display device, wherein the test image comprises at least two separate fields, with one of the fields having a first test pattern and another one of the fields having a control pattern, wherein the test pattern is configured to be stimulus for the user once the test pattern is recognizable by the user; then (c) detecting whether an eye movement toward the test pattern occurs, a presence of an eye movement toward the test pattern confirming the discernibility of the first test pattern by the user; then (d) repeating steps (b) and (c) with a further test pattern, with the further test pattern being more difficult to discern than the first test pattern; and (e) determining the visual acuity of the user from the occurrence or the absence of the eye movement toward the first test pattern and to at least one further test pattern.

U.S. 2015/070273 A1 discloses methods and apparatuses for optical detection and tracking of an eye movement. A method for tracking the eye movement comprises emitting light toward the eye of the user using a plurality of light sources substantially equally spaced from a photodetector module of the apparatus, receiving module at the photodetector an at least partial retroreflection of the light emitted by each of the plurality of light sources and retroreflected from the eye, and determining a positional parameter of the eye on the basis of different values of the at least partial retroreflection of the light in relation to the plurality of light sources.

DE 10 2012 022 662 A1 discloses an apparatus and a method for checking the human ability to see, comprising an image generation module for generating any desired test images, an imaging module which serves to image the test image provided by the image generation module as a stimulus on the retina of the eye, wherein the imaging module contains at least one optical component with the variable focal length such that the test image of the image generation module is perceivable from virtually produced and variable distances by the eye, an accommodation measuring device for measuring the accommodation of the eye, a line-of-sight measuring device for measuring the line of sight of the eye, a control and evaluation module which captures and/or further processes the information and/or measurement values originating from the individual modules and/or controls the operating procedure. The apparatus is distinguished in that a stimulation of the accommodation of the eye is implementable by means of the respective test image and/or by means of the line of sight, the measurement of the accommodation of the eye and the line of sight of the eye is implementable in simultaneous or alternating fashion, and the measurement values of the accommodation of the eye and of the line of sight of the eye are feedable to a control and evaluation module. A simultaneous check of both eyes with a generation of virtual binocular images, which for example cannot be distinguished from visual reality from a vision-physiological point of view, can be carried out in a special configuration of the apparatus.

WO 2009/007136 A1 discloses a method for checking and/or determining user data of a spectacle lens user, including the steps of: providing subjective data of a spectacle lens user, the subjective data comprising at least subjective refraction data; providing objective refraction data of the spectacle lens user; comparing at least a subset of the subjective refraction data to at least a subset of the objective refraction data and determining a comparison result; adjusting at least the subset of the subjective refraction data to the objective refraction data on the basis of the comparison result under the precondition that the comparison result satisfies at least one predetermined comparison condition, otherwise keeping at least the subset of the subjective refraction data and/or providing a notification containing the comparison result.

Published European patent application EP 3730037 A1 discloses a method for determining a refractive error of an eye of a user. To this end, a symbol is represented on a visual display unit, wherein a parameter of the symbol represented on the visual display unit is altered, an eye movement metric of the eye of the user is captured depending on the symbol represented on the visual display unit, a point in time is determined, at which a recognition threshold of the user for the symbol represented on the visual display unit arises from the eye movement metric of the eye of the user, and a value for the refractive error of the eye of the user is determined from the parameter set at that point in time.

Published European patent application EP 3756534 A1 discloses a method and an apparatus for determining a contrast sensitivity threshold of eyes of a user. To this end, eye movements which by a stimulus configured to excite an optokinetic nystagmus are recorded and evaluated.

SUMMARY

In particular proceeding from the disclosure of U.S. 2012/0287398 A1, it is the object of the present disclosure to provide methods and apparatuses for jointly determining accommodation and vergence of at least one eye of a user, for determining an accommodation of at least one eye of a user, for determining values for a control of myopia of at least one eye of the user, and for producing a spectacle lens for the user, data processing apparatuses and associated computer programs, computer-readable data media, data medium signals and computer-readable media, which at least partly overcome the listed disadvantages and restrictions of the related art.

In particular, the apparatuses, methods and computer programs are intended to facilitate the joint determination of the accommodation and the vergence of at least one eye of the user, typically of both eyes of the user, and the control of myopia of at least one eye of the user, typically of both eyes of the user, without having to resort to a subjective estimate by appropriately trained staff.

Furthermore, the joint determination of the accommodation and the vergence of at least one eye of the user, typically of the eyes of the user, should be able to serve as a basis for an effective control of myopia, specifically both for first care of the user and for monitoring progress, in particular in view of potential myopia progression in the user.

This object is achieved by the methods, computer programs, and apparatuses for jointly determining the accommodation and the vergence of the at least one eye, as taught herein. Exemplary embodiments, which can be realized individually or in combination, are discussed below.

Hereinafter the terms "exhibit," "have," "comprise," or "include" or any grammatical deviations therefrom are used in a non-exclusive way. Accordingly these terms can refer either to situations in which, besides the feature introduced by these terms, no further features are present, or to situations in which one or more further features are present.

In a first aspect, the present disclosure relates to a method for jointly determining accommodation and vergence of at least one eye of a user. The method comprises the following steps a) to d), typically in the stated sequence. Another sequence is also possible in principle. In particular, the steps could also be performed entirely or partially at the same time. It is furthermore possible for individual, multiple, or all steps of the method to be performed repeatedly, in particular more than once. In addition to the stated steps, the method can also comprise further method steps.

The method for jointly determining accommodation and vergence of at least one eye of a user comprises the steps of:
a) presenting at least one symbol at at least one first distance in front of at least one eye of a user for stimulating the accommodation of the at least one eye;
b) capturing at least one eye movement of the at least one eye;
c) determining a refraction of the at least one eye with the accommodation of the at least one eye at the at least one first distance; and
d) jointly determining the accommodation and the vergence of the at least one eye by
determining a change in the refraction of the at least one eye with the accommodation of the at least one eye at the at least one first distance in relation to the accommodation of the at least one eye at at least one second distance; and
determining the vergence of the at least one eye from the at least one eye movement of the at least one eye with the accommodation of the at least one eye at the at least one first distance.

Typically, the accommodation and the vergence of the eyes of the user are determined, particularly typically simultaneously, by means of the method listed above.

In an exemplary embodiment, the individual steps of the method, listed above, for determining the accommodation and the vergence of at least one eye of a user are carried out with the aid of at least one mobile terminal. Typically, at least one mobile terminal should be understood to mean an apparatus which comprises at least one programmable processor and at least one camera and at least one acceleration sensor, and which is typically designed to be carried, i.e., configured in respect of dimensions and weight so that a person is capable of carrying it along. Further components can be present in the at least one mobile terminal, for example at least one visual display unit, at least one light source for, e.g., visible light from a wavelength range of 380 nm to 780 nm and/or infrared light from a wavelength range of 780 nm to 1 mm and/or at least one light receiver with a sensitivity to, e.g., visible light from a wavelength range from 380 nm to 780 nm and/or infrared light from a wavelength range from >780 nm to 1 mm. Typical examples of such mobile terminals are smartphones or tablet PCs, which may comprise at least one visual display unit, for example a sensor screen (touchscreen), at least one camera, at least one accelerometer, at least one light source, at least one light receiver and further components such as wireless interfaces for mobile radio or WLAN (wireless LAN). The presentation of at least one symbol at at least one first distance in front of at least one eye of a user for the purposes of stimulating the accommodation of the at least one eye as per step a) of the method according to the disclosure can be implemented, for example, by means of the at least one visual display unit of the at least one mobile terminal. Capturing an eye movement of the at least one eye as per step b) of the method according to the disclosure can be implemented for example by means of the at least one camera or by means of the at least one light source and by means of the at least one camera or the at least one light receiver, in each case of the at least one mobile terminal. Determining a refraction of the at least one eye with the accommodation of the at least one eye at the at least one first distance as per step c) of the method according to the disclosure can be implemented for example by means of the at least one camera or by means of the at least one light source and by means of the at least one camera or the at least one light receiver, in each case of the at least one mobile terminal. Jointly determining the accommodation and the vergence of the at least one eye by
a) determining a change in the refraction of the at least one eye with the accommodation of the at least one eye at the at least one first distance in relation to the accommodation of the at least one eye at a second distance; and
b) determining the vergence of the at least one eye from the at least one eye movement of the at least one eye with the accommodation of the at least one eye at the at least one first distance,
as per step d) of the method according to the disclosure can be implemented for example by means of the at least one camera or by means of the at least one light source and by means of the at least one camera or the at least one light receiver, in each case of the at least one mobile terminal.

The term "accommodation" relates to an adjustment of the refraction of at least one eye of a user when imaging an object, situated in principle at any distance in front of at least one eye of the user between the near point and the far point, on the retinal plane of the at least one eye. In this case, the "far point" relates to an endpoint of a refraction direction of the at least one eye of the user in the unaccommodated state. Within the scope of the present disclosure, the term "accommodation" also comprises the unaccommodated state, which is stimulated by means of at least one symbol situated at the far point. In contrast thereto, the "near point" denotes a point specifying the shortest distance in front of the at least one eye of the user at which the object can still be imaged in focus on the retinal plane of the at least one eye, with the near point representing an individual variable dependent, in particular, on the age of the user. A defined point on the at least one eye, in particular on the cornea, for example a location of an observable corneal reflection, can serve as a reference point for the measurement of the distance.

Here, the term "refraction" denotes a refraction of light in the at least one eye of the user which is experienced by a light beam incident in the interior of the at least one eye through the pupil. Defocusing of the at least one eye of the user can lead to a refractive error (ametropia) of the user, in particular to nearsightedness (myopia) or farsightedness (hyperopia). For the subjective determination of the refraction known from the related art, optotypes, typically in the form of numerals, letters or symbols, are usually provided on a board or a visual display unit with a defined size for a given distance and are observed by the user. By having available a number of optical lenses with known properties and by guiding the user through a defined questionnaire process, it is possible to subjectively determine the defocusing of the at least one eye of the user and to determine which refractive configuration of the spectacle lens leads to a substantial compensation of the defocusing of the at least one ametropic eye of the user and hence to an image quality for the user that is as optimal as possible. In this case, the term "a pair of spectacles" denotes any element which comprises two individual spectacle lenses and a spectacle frame, the spectacle lens being provided for insertion into a spectacle frame that is selected by a wearer of the pair of spectacles. Instead of the term "wearer" used here, one of the terms "subject," "spectacle wearer," or "user" can also be used synonymously.

The term "vergence" denotes opposing eye movements of the two eyes of a pair of eyes of the user, wherein each of the two eyes carries out an eye rotation in a respectively opposite direction of rotation about mutually parallel axes. In this case, each of these mutually parallel axes respectively represents a continuation to infinity of the connecting line between the center of the pupil of an eye and the center of rotation of the latter. In this case, the center of rotation of the eye is the geometric center of rotation of the eye. The term "vergence" includes both the opposing eye movement of the two eyes of a pair of eyes of the user toward the center line and also the opposing eye movement of the two eyes of a pair of eyes of the user divergently away from the center line. The center line denotes the perpendicular projection to infinity at half the interpupillary distance perpendicular to the path of the interpupillary distance. The center of the pupil is the geometric center point of the pupil.

The term "vergence" furthermore denotes the eye movement of at least one eye of the user from the axis representing the continuation of the connecting line to infinity between the center of the pupil of an eye and the center of rotation of the latter, both toward the center line and divergently away from the latter. Furthermore, the term "vergence" also comprises eye movements of the two eyes of a pair of eyes of the user, wherein each of the two eyes independently of one another carries out an eye rotation about its respective axis, which represents the continuation to infinity of the connecting line between the center of the pupil of an eye and the center of rotation of the latter, both toward the center line and divergently away from the latter. In all of the explanations regarding vergence and divergence of the two eyes specified above, the absolute value of the eye rotation can have a different manifestation in both eyes. This different manifestation can be present both when the eye rotation of both eyes is vergent or divergent and when the eye rotation of one of the two eyes is vergent and the eye rotation of the other eye is divergent.

As already mentioned at the outset, the accommodation and the vergence of the at least one eye of the user, typically of the pair of eyes of the user, cannot be considered completely independently of one another. For a defined accommodation outlay, this is respectively connected to a corresponding vergence outlay. Rather, a reduction of an accommodation error by means of progressive addition lenses depends significantly on a chosen addition power. Likewise, an inaccuracy of the accommodation of myopic subjects exceeds that of non-myopic subjects. Furthermore, the absolute value of the vergence set for a certain accommodation distance (also abbreviated "AC/A," for accommodative convergence accommodation) is higher for myopic subjects than the actually required absolute value, and so the resultant error is greater than in the case of non-myopic subjects. Moreover, the term "vergence" in conjunction with the present disclosure also relates to what is known as "divergence," which occurs when the distance is changed from the near point to the far point, within the scope of which the eyes likewise carry out an opposing rotational movement divergently away from the center line, about mutually parallel axes, or within the scope of which the eyes carry out a mutually independent eye rotation divergently away from the center line, about the respective axis of the eye. Further, the term "vergence" also comprises a "divergence" which occurs when the distance is changed from the near point to the far point and at least one eye of the user carries out an eye movement divergently away from the center line, about the axis which represents the continuation of the connecting line to infinity between the center of the pupil of an eye and the center of rotation of the latter. In this case, too, axis as defined above respectively represents the continuation to infinity of the connecting line between the center of the pupil of an eye and the center of rotation of the latter. In this case, too, the center line as likewise already defined above respectively is the perpendicular projection to infinity at half the interpupillary distance perpendicular to the path of the interpupillary distance.

According to the disclosure, the two variables of accommodation and vergence of one or both eyes of the user are determined together, in particular in order to determine, as exactly as possible, the ratio AC/A, which is defined by the absolute value of the vergence independently set by the at least one eye for a certain accommodation distance. In this case, the terms "determining" and "determination" denote a calculation of a value which can be derived from at least one measurement variable capturable by measurement, which is connected to the value, in particular using an evaluation unit. The term "capturing" refers in this case to recording the at least one measurement variable capturable by measurement, from which the desired value can be derived, in particular using the evaluation unit. In this case, the term "joint" denotes the determination of the two measurement variables with a tight temporal relationship, typically using the measurement variables captured by the same apparatus, particularly typically with a temporal relationship, in particular simultaneously or immediately successively. In this way, the aforementioned tight relationship between accommodation and vergence can according to the disclosure be mapped by measurement.

According to step a) of the present method there is a presentation of at least one symbol at at least one first distance in front of an eye of a user for stimulating the accommodation of the eye. In this case, the term "symbol" relates to optotypes, in particular letters, numbers or signs; images or patterns, each of which can be represented in color or in black and white. While the "optotype" is an individual fixed symbol in each case, which is only able to be varied to a restricted extent in its proportions for recognition by the user, the term "pattern" denotes any graphical structure which—in particular in contrast to noise which remains without identifiable structure—has at least one spatially oriented period, within which the structure of the pattern is typically represented repeatedly. Therefore, instead of the term "pattern" it is then also possible to use the term "periodic pattern" in order to clearly express this property of the pattern, with both terms herein comprising the same content.

The presentation of the at least one symbol can be implemented in monocular fashion, in each case separately for one eye. Alternatively, the at least one symbol can be presented jointly in binocular fashion and simultaneously for both eyes of a pair of eyes. In this case, the presentation of the at least one symbol can be implemented in different ways, in particular on a visual display unit which can be arranged at a fixed but selectable distance in front of the at least one eye of the user. Here, the term "visual display unit" denotes an electronically controllable display with a two-dimensional extent, with the desired at least one symbol being representable with largely freely selectable parameters at any location within the extent. In this case, the visual display unit can typically be selected from a monitor, a screen or a display, wherein the visual display unit can be driven by the evaluation unit. In this case, the visual display unit can be configured to be looked at or, typically, to be looked through. In this case, the visual display unit can typically be contained in a mobile communications device. In this case, the term "mobile communications device" encompasses in particular a cellular phone (cellphone), a smartphone or a tablet. However, other types of mobile communications devices are conceivable. In this way, the present method for jointly determining accommodation and vergence of one eye or both eyes of a user can be carried out at any desired location. However, other types of visual display units are likewise possible.

In an alternative configuration, the at least one symbol can be presented by means of a projection device. In this case, the projection device can be configured to project the at least one symbol to a predetermined location in space, which corresponds to the fixed but selectable distance in front of the at least one eye of the user, wherein the projection device can be driven by the evaluation unit. Alternatively or in addition, the at least one symbol can be projected onto the at least one eye of the pair of eyes in such a way that the user can recognize the at least one symbol virtually at the predetermined location in space, which corresponds to the fixed but selectable distance in front of the at least one eye of the user. Further configurations for representing the at least one symbol at the desired distance in front of the at least one eye of the user are conceivable, however.

On account of electronic control, in particular using the evaluation unit, a parameter of the presented at least one symbol can be varied easily and over a broad scope. The "parameter" can be a property of the at least one symbol, depending on the selected symbol, in particular an extent, an orientation, a position, a frequency, a contrast or a color (including black and white). In the case of the pattern a structure can be represented repeatedly, wherein similar points or regions can form over the structure of the pattern as a result of repetition. Typical configurations of similar points or regions can typically be present as periodic maxima or minima of the pattern. While the selected parameters of a conventional optotype, in particular a letter, a number or a sign, can therefore be an extent of the symbol, in particular a height or width, the parameter in the case of the periodic pattern typically relates to a parameter of a periodic function, in particular a repetition frequency. In this case, the "periodic function" denotes an instruction for a configuration of a temporally repeated, or typically spatially repeated, variation of the pattern. The periodic function can typically be selected from a sine function, a cosine function or a superposition thereof. However, other periodic functions are conceivable.

In a typical configuration, the presented at least one symbol can be a pattern, wherein the associated parameter of the pattern comprises at least a spatial frequency of the periodic pattern. In this case, the term "spatial frequency" denotes a reciprocal of a spatial distance between two adjacently arranged similar points, in particular a maximum or a minimum, in a spatially periodic change in the pattern, and it can be specified in units of 1/m or, in particular if a distance from the at least one eye of the user is known, it can alternatively or additionally also be specified as a dimensionless number, for example per degree or per cycle. Other ways of determining the spatial frequency from the pattern are conceivable however, for example from a spacing of points of equal intensity.

In this typical configuration, the periodic pattern can be designed as a two-dimensional superposition of a periodic function, in particular the sine function, which can extend in a first direction and a constant function which can extend in a second direction, which second direction can typically be arranged to be perpendicular to the first direction. In this case the term "perpendicular" denotes an angle of 90°±30°, typically 90°±15°, particularly typically 90°±5°, in particular 90°±1°, in each case in relation to the first direction. However, other angles between the first direction and the second direction are likewise possible. In this way, the pattern can be present in the form of stripes arranged next to one another in periodic fashion, which can also be referred to as the "sinusoidal grating" or "Gabor patch." The term "Gabor patches" refers to sinusoidal gratings which are typically provided with a Gaussian envelope and known to be usable in particular as a stimulus for at least one eye of the user. However, other types of patterns are possible.

According to step b), an eye movement of the at least one eye is captured. According to the disclosure, capturing an eye movement, typically at least one selected eye movement metric, in particular using the evaluation unit, serves to determine the sought-after vergence by virtue of
a) opposing eye movements of the two eyes of a pair of eyes of the user, wherein each of the two eyes carries out an eye rotation in a respectively opposite direction of rotation, both toward the center line and divergently away from the latter, about mutually parallel axes, which each represent a continuation to infinity of the connecting line between the center of the pupil of an eye and the center of rotation of the latter, or
b) the eye movement of at least one eye of the user from the axis representing the continuation of the connecting line to infinity between the center of the pupil of an eye and the center of rotation of the latter, both toward the center line and divergently away from the latter, or
c) eye movements of the two eyes of a pair of eyes of the user, wherein each of the two eyes independently of one another an eye rotation about its respective axis, which represents the continuation to infinity of the connecting line between the center of the pupil of an eye and the center of rotation of the latter, both toward the center line and divergently away from the latter, being captured and evaluated in each case. The center of rotation of the eye is the geometric center of rotation of the eye. The center line is the perpendicular projection to infinity at half the interpupillary distance perpendicular to the path of the interpupillary distance. In all of the explanations regarding vergence and divergence of the two eyes specified above, the absolute value of the eye rotation can have a different manifestation in both eyes. This different manifestation can be present both when the eye rotation of both eyes is vergent or divergent and when the eye rotation of one of the two eyes is vergent and the eye rotation of the other eye is divergent.

In a typical configuration of the present disclosure it is possible, as explained in more detail below, for the capturing of an eye movement moreover also to serve the determination of the refraction of the at least one eye as per step c), for the purpose of which, for example, use can be made of the method disclosed in EP 3730037 A1, or typically at least one refraction measuring device selected from the group comprising at least one Shack-Hartmann aberrometer, at least one off-centered photorefractor and at least one autofocus system. The refraction measuring device particularly typically comprises at least one Shack-Hartmann aberrometer. In this case, a Shack-Hartmann aberrometer can be used as an optical sensor which for example can comprise at least one microlens array and at least one camera sensor, and serves to capture the refraction and higher-order aberrations of the at least one eye. An off-centered photorefractor likewise serves as an optical sensor for capturing at least one light reflection, wherein the photorefractor may comprise at least one camera sensor and, optionally, a light source, for example an infrared light source, arranged off center. Typically, the photorefractor comprises at least one camera sensor and a light source arranged off center. The refraction of the at least one eye can be calculated from the at least one light reflection. To generate the at least one light reflection, the light source need not be a constituent part of the off-centered photorefractor, but can also be arranged independently thereof. An autofocus system also serves as an optical sensor for capturing the refraction of the at least one eye, wherein the refraction is determined by the optimization of at least one optical quality, typically the image sharpness and/or the image contrast, on at least one camera sensor. The optimization is typically implemented by means of different optical focus settings and an evaluation of the optical quality of the camera recordings captured for the respective optical focus setting by the at least one camera sensor. Furthermore, the at least one refraction measuring device may comprise at least one lens and/or at least one stop. The at least one refraction measuring device typically comprises at least one off-centered photorefractor or at least one autofocus system and can for example be a constituent part of at least one mobile terminal or be connected to at least one mobile terminal, for example in the form i) of at least one camera or ii) of at least one light source and at least one camera or at least one light receiver, in each case of the at least one mobile terminal.

In this case the term "eye movement metric" denotes a measure linked to a movement of the at least one eye of the user, wherein the movement of the at least one eye of the user is caused by the external stimulus in the form of at least one symbol that acts on the at least one eye of the user. Within the scope of the present disclosure, the eye movement metric can typically relate to: opposing eye movements of the two eyes of a pair of eyes of the user, wherein each of the two eyes carries out an eye rotation in a respectively opposite direction of rotation, both toward the center line and divergently away from the latter, about mutually parallel axes, which each represent a continuation to infinity of the connecting line between the center of the pupil of an eye and the center of rotation of the latter; eye movements of at least one eye of the user from the axis representing the continuation of the connecting line to infinity between the center of the pupil of an eye and the center of rotation of the latter, both toward the center line and divergently away from the latter; eye movements of the two eyes of a pair of eyes of the user, wherein each of the two eyes independently of one another an eye rotation about its respective axis, which represents the continuation to infinity of the connecting line between the center of the pupil of an eye and the center of rotation of the latter, both toward the center line and divergently away from the latter; a pursuit eye movement; an eye movement relating to microsaccades comprising a microsaccade direction, a microsaccade rate or a saccade accuracy; or an optokinetic nystagmus. Further eye movement metrics could for example include a dwell time when the at least one represented symbol is read fluently, which is also referred to as "fixation duration." Moreover, further types of eye movements can likewise be captured. What type of eye movement metric or which combination of at least two eye movement metrics is used depends essentially on an accuracy of a device used to this end, and on the respective use purpose. While opposing eye movements of the two eyes of a pair of eyes of the user, wherein each of the two eyes an eye rotation in a respectively opposite direction of rotation, both toward the center line and divergently away from the latter, about mutually parallel axes, which each represent a continuation to infinity of the connecting line between the center of the pupil of an eye and the center of rotation of the latter, eye movements of at least one eye of the user from the axis representing the continuation of the connecting line to infinity between the center of the pupil of an eye and the center of rotation of the latter, both toward the center line and divergently away from the latter, or mutually independent eye movements of the two eyes of a pair of eyes of the user, wherein each of the two eyes independently of one another an eye rotation about its respective axis, which represents the continuation to infinity of the connecting line between the center of the pupil of an eye and the center of rotation of the latter, both toward the center line and divergently away from the latter, can each be used to determine the vergence in particular, pursuit eye movements can typically be suitable for determining the refraction.

In this case, the term "pursuit eye movement" denotes a movement of the at least one eye with which the at least one eye pursues the movements of the presented symbol fixated on by the at least one eye. In general, the pursuit eye movement is a slow movement of the at least one eye with an angular speed of 0.5°/s to 50°/s, during which an image representation of the symbol typically remains on the fovea of the at least one eye. The pursuit eye movements cannot be produced voluntarily but require the presented symbol to carry out a movement which the at least one eye of the user can pursue.

Within the scope of the present disclosure eye movement metrics based on saccades or microsaccades can typically be used as a measure of establishing whether or not the user has recognized the presented symbol as a stimulus. The term "saccade" denotes jerky visual target movements of the at least one eye of the user which are carried out in target-related fashion, which have a small amplitude of at least 1° and which in particular serve the purpose of a fast regular realignment of a line of sight of the at least one eye on a fixation point, typically by virtue of the image representation of a symbol situated on the fixation point being displaced from a periphery to the fovea of the at least one eye. A "saccade rate" is typically 1 Hz to 5 Hz, wherein an angular speed of 5°/s to 500°/s can be achieved. The term "microsaccade" denotes small jerky and involuntary visual movements which may not be related to a target, which occur randomly and whose amplitude is less than 1°. The "microsaccade direction" relates to a spatial orientation of the microsaccade relative to a coordinate system, typically a coordinate system established by the presented symbol. In this case, the orientation relative to the presented symbol can serve as a measure of recognition. The "saccade accuracy" denotes a spatial precision of a realignment relative to a new position of a stimulus. If the perception of the stimulus following the realignment is poorer, an expected error of the realignment is greater in this case.

As an alternative or in addition, eye movement metrics which relate to the optokinetic nystagmus can typically be used as a measure of establishing whether or not the user has recognized the presented symbol as a stimulus. The term "optokinetic nystagmus" denotes a physiological eye movement reflex which is characterized by a slow and a quick phase. In this case, the slow phase corresponds to a pursuit movement at the speed of a moving stimulus in the surroundings. A correlation of the phase or the speed of the stimulus with the slow phase of the optokinetic nystagmus can be used as a measure of whether a user recognizes the stimulus. Further, it is conceivable to use a correlation of the phase or the speed of the stimulus with the fast phase of the optokinetic nystagmus as a measure of whether a user recognizes the stimulus.

To capture the eye movement metrics, it is possible to use an eye movement measuring device, which is also referred to as an "eyetracker" and which is controlled using the evaluation unit in particular. The eye movement measuring device can typically comprise a camera, particularly typically a video camera, in particular in order to be able to carry out video-based "eye tracking" by virtue of typically recording image sequences of an eye area of the user and evaluating these by means of image processing in order to establish at least one of the eye movement metrics therefrom. To this end, known algorithms in particular can be used in each case. Moreover, image processing, in particular using the evaluation unit, can furthermore be used to determine geometric data of the at least one eye, typically its pupil, in particular the position and diameter of its pupil, from the recorded image sequences, and from this it is possible to determine the line of sight of the at least one eye, for example. To this end, it is possible, in particular using the evaluation unit, to use methods which include selected reflection points that may arise on the front side and/or back side of the cornea and lens if the at least one eye is irradiated by a light source. In particular it is possible to determine a line of sight from a corneal reflection and pupil position; see for example P. Blignaut, *Mapping the Pupil-Glint Vector to Gaze Coordinates in a Simple Video-Based Eye Tracker*, Journal of Eye Movement Research 7(1):4, pages 1-11, 1995. However, in principle, it is also possible to record other reflections, in particular by means of a so-called "dual Purkinje eyetracker." Since the corneal reflection does not move without a head movement, but the pupil changes its position during the eye movement, the eye rotation can be deduced therefrom. Here, the "pupil" denotes an entry opening that is present in each eye, through which radiation in the form of light can enter into the interior of the eye. In the opposite direction, the pupil can be regarded as an exit opening, through which the line of sight of the user from the eye to the surroundings can be defined.

Furthermore, provision can be made of an illumination device, in particular in order to be able to capture the eye movement metric of the user with the highest possible resolution and the highest possible contrast by means of the camera, in particular the video camera. As an alternative or in addition, it is possible to resort to daylight or lighting already present. In this case, the illumination device can be configured as a light source which can be comprised by the eye movement measuring device or which can be set up as a separate device.

In a particular configuration, the camera, in particular the video camera, can have a sensitivity in the infrared spectral range, i.e., at a wavelength of 780 nm to 1 mm, typically of 780 nm to 3 µm, in particular of 780 nm to 1.4 µm (according to DIN EN ISO 13666:2013-10 section 4.4, also referred to as "IR-A"). In order to provide infrared radiation, the light source provided to this end can emit in the infrared spectral range, in particular at a wavelength for which the camera has a sufficient sensitivity. The light source can typically be selected from a micro-incandescent lamp, a solid state-based IR emitter, a light-emitting diode or an infrared laser, wherein appropriate filters can be used.

According to step c) there is an determination of a refraction of the at least one eye with the accommodation of the at least one eye at the at least one first distance. As explained in more detail below, the refraction of the at least one eye can be determined using a refraction measuring device configured to capture the refraction of the at least one eye, wherein the refraction measuring device can be controlled, in particular, using the evaluation unit. In this case, for example as disclosed in U.S. 2012/0287398 A1, the refraction measuring device may comprise a number of optical elements configured to determine the defocusing of the at least one eye of the user. A typical configuration of the refraction measuring device is presented with reference to FIG. 2 in the exemplary embodiments. However, other ways of configuring the refraction measuring device are possible.

In an alternative configuration, the refraction of the eye can be implemented by means of capturing the eye movement of the at least one eye of the user, typically during as per step b). As disclosed in EP 3730037 A1, capturing the eye movement of the at least one eye of the user, in particular using the evaluation unit, on the basis of the symbol can be implemented while a parameter of the symbol is altered, wherein it is possible to determine a point in time at which a recognition threshold of the user for the symbol emerges from the eye movement, wherein it is possible to establish the refraction of the at least one eye from the parameter for the symbol defined at that point in time. In this case, capturing the eye movement can be repeated for various values of the parameter typically until the desired point in time has been determined. In this case, the term "recognition threshold" denotes the fact that the user can only just still or only just perceive the presented symbol as a stimulus for the at least one eye. If one of the parameters of the symbol, in particular the spatial frequency in the periodic pattern, increasingly increases, it is possible in the process to establish the point in time at which the symbol just can no longer act as a stimulus for the at least one eye of the user. Conversely, if one of the parameters of the symbol, in particular the spatial frequency in the periodic pattern, increasingly decreases, it is possible in the process to establish the point in time at which the presented symbol for the first time cannot act as a stimulus for the at least one eye of the user. Alternatively, even if, for example, one of the parameters of the symbol, in particular the spatial frequency in the periodic pattern, increasingly decreases, it is possible in the process to establish the point in time at which the presented symbol for the first time can just act as a stimulus for the at least one eye of the user. Conversely in this case, if one of the parameters of the symbol, in particular the spatial frequency in the periodic pattern, increasingly increases, it is possible in the process to establish the point in time at which the presented symbol for the first time can act as a stimulus for the at least one eye of the user.

In a special configuration of the present disclosure the point in time at which the recognition threshold of the user for the presented symbol is evident from the reaction of the user can be established by virtue of the fact that the eye movement metric of the user only just still follows or only just starts to follow the movement of the presented symbol. In particular, the pursuit eye movement of the user with which they follow the movements of a symbol which is fixated by the at least one eye can be used to this end to establish the desired point in time, in particular since, as mentioned above, the pursuit eye movements cannot be generated voluntarily but follow the movement of the presented symbol which serves as a stimulus for the at least one eye of the user. In the process, it is possible to establish the desired point in time, at which the recognition threshold of the user for the presented symbol, in particular the spatial frequency of the pattern, from the eye movement metric of the user. To this end, data for capturing the eye movement of the user which were recorded by the video camera can typically be used to determine the line of sight of the user to the presented symbol. In the case of an increasing reduction in one of the parameters of the symbol, in particular in the spatial frequency in the periodic pattern, the pursuit eye movement of the user will correspond to the movement of the symbol for as long as the user can recognize the presented symbol. Once a point in time has been reached at which the user just can no longer recognize the presented symbol, in particular the periodic pattern, and said symbol can consequently no longer act as a stimulus for the at least one eye of the user, the pursuit eye movement of the user will deviate from the movement of the symbol. Conversely, if the point in time is reached at which the user for the first time can just recognize the presented symbol, in particular the periodic pattern, and said symbol can consequently for the first time act as a stimulus for the at least one eye of the user, the pursuit eye movement of the user will now start to follow the movement of the symbol. Independently of the type of configuration it is preferable in this context to set a threshold by means of which a degree of deviation of the pursuit eye movement of the user from the movement of the symbol is established as the sought-after point in time. The point in time at which the deviation exceeds or drops below the defined threshold in this case represents the sought-after point in time.

A value for the refraction of the at least one eye of the user can be determined from the value of the parameter used at the established point in time to set the selected parameter of the symbol, this typically being implemented following the establishment of the point in time. Here, in the above-described configuration the value for the refraction can be determined from the spatial frequency of the pattern, which may also be a limit frequency of the pattern, established at the point in time, for which spatial frequency the recognition threshold of the user for the presented symbol is evident from the observation of the eye movement metric of the user. The "limit frequency" denotes the spatial frequency of the pattern at which the contrast sensitivity becomes zero or the contrast of the stimulus becomes maximal. This frequency can also be considered to be the resolution limit of the visual system. In this case the term of "contrast sensitivity" of the at least one eye defines a measure for distinguishing different shades of gray as the reciprocal of the smallest, just still perceivable difference between two grayscale values. The terms "visual acuity" and "visual discrimination" of the at least one eye of the user in each case specify a measure for a spatial distance between two points which the at least one eye of the user can still perceive as distinguishable. In the above-described configuration the contrast sensitivity can be determined by means of a periodic pattern in the form of stripes arranged periodically next to one another, said pattern also being referred to as "sinusoidal grating" or as "Gabor patch." As described in A. Leube et al., *Individual neural transfer function affects the prediction of subjective depth of focus*, Scientific Reports 2018, 8(1), 1919, Gabor patches whose contrast is reduced until no stripe pattern can be perceived any more are typically used to this end. This contrast value is used as the recognition threshold. This procedure is repeated for various spatial frequencies. For further details, reference is made to the exemplary embodiments.

Independently of the type of determination of the refraction occurring on part of the user, a spherocylindrical lens can be determined therefrom, which spherocylindrical lens, as a spectacle lens, can be used to compensate the refractive error, bringing about defocusing, of the at least one eye in such a way that an image quality that is as optimal as possible can be obtained for the user. Different modes of expressions are suitable for describing the spherocylindrical lens. The DIN EN ISO 13666:2013-10 standard, also referred to as "standard" below, defines in section 11.2 what is known as a "spherical power," which is defined as a value for a vertex power of a spectacle lens with spherical power or for the respective vertex power in one of two principal meridians of the spectacle lens with astigmatic power. According to the standard, 9.7.1 and 9.7.2, the "vertex power" is defined as the reciprocal of a paraxial back vertex focal length, in each case measured in meters. The spherocylindrical spectacle lens with astigmatic power in accordance with the standard, section 12, combines a paraxial, parallel beam of light in two separate focal lines perpendicular to one another and therefore has a spherical vertex power only in the two principal meridians. The "astigmatic power" is here defined by cylindrical power and cylinder axis. In this case, the "cylindrical power" in accordance with the standard, 12.5, represents the absolute value of an "astigmatic difference," which indicates the difference between the vertex powers in the two principal meridians. In accordance with the standard, 12.6, the "cylinder axis" denotes a direction of the principal meridian whose vertex power is chosen as a reference value. Finally, according to the standard, 12.8, the "power" of the spectacle lens with astigmatic effect is specified by means of three values, comprising the vertex powers of each of the two principal meridians and the cylindrical power. Furthermore, the spherocylindrical lens can be described by specifying a "refraction vector" (power vector) as per L. N. Thibos, W. Wheeler and D. Horner (1997), *Power Vectors: An Application of Fourier Analysis to the Description and Statistical Analysis of Refractive Error*, Optometry and Vision Science 74 (6), pp. 367-375. The power vector, which can be described by exactly one point in a three-dimensional dioptric space, wherein the three-dimensional dioptric space can be spanned by coordinates, corresponds to or correlates with the mean spherical refraction and the cylindrical power and its associated cylinder axis.

According to step d), the joint determination of the accommodation and the vergence of the at least one eye, in particular using the evaluation unit, is implemented by, firstly, determining a change in the refraction of the at least one eye with the accommodation of the at least one eye at the at least one first distance in relation to the accommodation of the at least one eye at a second distance, and by, secondly, determining the vergence of the at least one eye from the eye movement of the at least one eye with the accommodation of the at least one eye at the at least one first distance. Particularly typically, the aforementioned variable "AC/A" can be determined in the process, that is to say the absolute value of the vergence which the at least one eye sets independently for a certain accommodation distance.

According to the disclosure there firstly is the determination of the change in the refraction of the at least one eye with its accommodation at the at least one first distance in relation to its accommodation at at least a second distance that differs therefrom. To this end, there is a change in a fixation of the at least one eye of the user from a second distance to a first distance, wherein the symbol presented as per step a), which is intended to be imaged as sharply as possible on the retinal plane of the at least one eye, is initially situated at the second distance and subsequently situated at the first distance. In this case, both the first distance and the second distance are located between the near point and the far point of the at least one eye, wherein in a typical configuration the at least one first distance can be selected for an accommodated state of the at least one eye and the second distance can be selected for an unaccommodated state of the at least one eye. Consequently, in a particularly typical embodiment of the present method, the determination of the refraction of the at least one eye of the user can be determined at at least two different distances of the presented symbol in front of the at least one eye.

For the at least two, typically at least three, at least four, at least five or at least six first or second distances, it is typically possible to select, firstly, values from 15 cm to 60 cm, particularly typically from 20 cm to 50 cm, in particular at approximately 20 cm, 25 cm, 40 cm and 50 cm, in which an accommodated state of the at least one eye is present, and, secondly, values of at least 1 m, typically at least 1.5 m, particularly typically at least 2 m in front of the at least one eye, which in this case assumes a substantially unaccommodated state. A different number of distances for which the refraction is determined and different values for the respectively chosen distances are possible, however. By determining values for the refraction at two or more mutually different first distances it is advantageously possible to obtain a measurement curve from which the change in the refraction can be evaluated with increased accuracy. However, different ways of determining the change in the refraction in the case of one of the changes in the first or second distance are conceivable.

In a special configuration which can typically be used, in particular, within the scope of monitoring the progress of the joint determination of accommodation and vergence of the at least one eye of the user over a period of time, for example over one or more weeks, over at least one month, at least one quarter or at least one year, it is possible to dispense with a current measurement of the refraction with the accommodation of the at least one eye at the second distance and instead use a known value for the refraction with the accommodation of the at least one eye at the second distance, typically from an earlier determination of this value, independently of whether this value was determined using the present method or any other method. An earlier determination of the value for the refraction of the at least one eye in the unaccommodated state using a conventional refractometer, for example as noted in a prescription for the user, may serve to this end. In this special configuration, it can consequently be enough at the relevant time to capture by way of measurement at least one value for the refraction with the accommodation of the at least one eye at the first distance and to resort to a known value for the refraction of the at least one eye with the accommodation at the second distance for the purposes of determining the change in the refraction of the at least one eye during step d).

Consequently, according to the disclosure the determination of the vergence of the at least one eye from the eye movement of the at least one eye with the accommodation of the at least one eye at the at least one first distance is implemented jointly. As already mentioned above, the term "vergence" denotes a) opposing eye movements of the two eyes of a pair of eyes of the user, wherein each of the two eyes carries out an eye rotation in a respectively opposite direction of rotation, both toward the center line and divergently away from the latter, about mutually parallel axes, which each represent a continuation to infinity of the connecting line between the center of the pupil of an eye and the center of rotation of the latter, or b) the eye movement of at least one eye of the user from the axis representing the continuation of the connecting line to infinity between the center of the pupil of an eye and the center of rotation of the latter, both toward the center line and divergently away from the latter, or c) eye movements of the two eyes of a pair of eyes of the user, wherein each of the two eyes independently of one another an eye rotation about its respective axis, which represents the continuation to infinity of the connecting line between the center of the pupil of an eye and the center of rotation of the latter, both toward the center line and divergently away from the latter.

Therefore, typically, the vergence of the at least one eye can be determined by way of capturing an eye rotation of the at least one eye during the accommodation of the at least one eye at the at least one first distance. In a particularly typical configuration it is possible to record the corneal reflection of the pupil of the relevant at least one eye. This is in particular advantageous as a result of the fact that the corneal reflection does not move without a head movement, but the pupil changes its position during the eye movement, and so the eye rotation can be reliably deduced therefrom. However, different ways of determining the vergence of the at least one eye, in particular the eye rotation, are conceivable. In particular, a movement of the iris of the relevant at least one eye or the aforementioned "dual Purkinje eyetracker" can be used.

In a further aspect, the present disclosure relates to a method for determining an accommodation of at least one eye of a user. In respect of configurations of this method, reference is made to the description of the method for jointly determining accommodation and vergence of at least one eye of a user.

In a further aspect, the present disclosure relates to computer programs comprising executable instructions for carrying out methods described herein. In respect of configurations of the computer programs, reference is made to the respective description of the associated method.

In further aspects, the present disclosure relates to data processing apparatuses, computer-readable data media, data medium signals and computer-readable media. In respect of configurations for these aspects, reference is made to the respectively associated subject matter of the data processing, of the data medium, of the data medium signal or of the computer-readable medium.

In a further aspect, the present disclosure relates to an apparatus for jointly determining accommodation and vergence of at least one eye of a user. According to the disclosure, the apparatus comprises a) a device configured to present a symbol at at least one first distance in front of at least one eye of a user for stimulating the accommodation of the at least one eye;

b) an eye movement measuring device configured to capture at least one eye movement of the at least one eye; and c) an evaluation unit configured to jointly determine the accommodation, from the change in the refraction, and the vergence, from the eye movement, in accordance with the method described herein.

In a typical configuration, the apparatus may comprise a refraction measuring device which is described elsewhere in this document and which is configured to capture the refraction of the at least one eye. In this case, the refraction measuring device can typically be selected from the group comprising at least one Shack-Hartmann aberrometer, at least one off-centered photorefractor and at least one autofocus system. For embodiment variants, different wavelengths and beam paths can be used in the process. Alternatively or in addition, the refraction of the at least one eye can be captured by means of the eye movement measuring device. In this context, reference is made to the corresponding illustration above or below.

In a further, typical configuration the apparatus can comprise a visual display unit as described elsewhere herein, the latter being configured to present the desired symbol at the at least one first distance and/or the second distance in front of the at least one eye. The visual display unit may be arranged in a movable but fixable manner, in particular in order to set the at least one first and/or second distance in a secure but selectable fashion. Alternatively or in addition, provision can be made for a projection device as presented above, the latter being configured to image the symbol on the at least one eye of the user. Typically, the projection device may have a Badal lens in this case for the purposes of imaging the symbol, with the Badal lens being arranged in front of the at least one eye of the user. The term "Badal lens" denotes an optical element comprising at least one lens and being configured to present the symbol always with the same angular size.

In a further, typical configuration, the evaluation unit can have a device for capturing a distance between the at least one eye of the user and the visual display unit or the camera. To this end, the pupil diameter of the at least one eye of the user can be determined from a determination of a pupil distance between the camera and the at least one eye of the user by way of image processing of an image sequence of the eye area of the user, in particular, which was recorded by the camera, particularly if a calibration of the pixels of the camera is present in spatial units. In a typical configuration, provision can be made of at least two cameras which are arranged jointly in the form of a stereo camera and are therefore configured for capturing the distance between the at least one eye of the user and the visual display unit. Alternatively or in addition, the apparatus can comprise a distance measuring unit configured for determining the pupil distance between the camera and the at least one eye of the user.

In a further typical configuration the apparatus may comprise two separate devices for presenting a symbol, two separate eye movement measuring devices and, optionally, two separate refraction measuring devices, which may be configured for the simultaneous, joint determination of the accommodation and the vergence of the two eyes of the user.

In respect of definitions and optional configurations of the apparatus including the features listed therein, reference is made to the description in this document of the method for jointly determining the accommodation and the vergence of the at least one eye of the user.

In an exemplary embodiment, the apparatus can be configured as at least one mobile terminal. In respect of definitions and optional configurations of the apparatus as at least one mobile terminal including the features listed therein, reference is made to the description in this document of the method for jointly determining the accommodation and the vergence of the at least one eye of the user by means of at least one mobile terminal.

While U.S. 2012/0287398 A1 is configured for determining the refraction of the eyes of a user, wherein monitoring of the vergence may optionally be provided, the present disclosure facilitates the joint determination of the accommodation and the vergence of one or both eyes of the user. Therefore, as described in more detail below, the method according to the disclosure and the proposed apparatus can be used in particular for the control of myopia for one or both eyes of the user and in the production of a spectacle lens or a contact lens for the eye or the eyes of the relevant user.

In a further aspect, the present disclosure relates to an apparatus for determining an accommodation of at least one eye of a user. In respect of configurations of this apparatus, reference is made to the description of the apparatus for jointly determining accommodation and vergence of at least one eye of a user.

In a further aspect, the present disclosure therefore relates to a method for determining values for a control of myopia of at least one eye of a user, wherein, to this end, the method described herein for jointly determining accommodation and vergence of the at least one eye of a user is used, wherein the jointly determined accommodation and vergence of the at least one eye of the user are used as the values for the control of myopia. In this case, there can be in particular optimized, individualized care of myopic subjects with individualized optical solutions for the control of myopia.

In a typical configuration, the present disclosure relates to a method for determining values for a control of myopia of the eyes of a user, wherein, to this end, the method described herein for jointly determining and particularly typically simultaneously determining accommodation and vergence of the eyes of a user is used, wherein the jointly determined and particularly typically simultaneously determined accommodation and vergence of the eyes of the user are used as the values for the control of myopia.

In a further typical configuration, the present disclosure relates to a method for determining values for a control of myopia of at least one eye of a user by means of at least one mobile terminal, wherein, to this end, the method by means of at least one mobile terminal described herein for jointly determining accommodation and vergence of the at least one eye of a user is used, wherein the jointly determined accommodation and vergence of the at least one eye of the user are used as the values for the control of myopia.

In a typical configuration, the proposed method and the apparatus presented herein can be used initially as a screening tool, also for example by using at least one mobile terminal, in order to estimate individual requirements of individual myopic users and the prospects of success in respect of reducing progression of the myopia by means of additional optical devices, in particular by means of progressive addition lenses. Within the scope of first care, parameters of the optical devices, for instance an addition power and a power of an inset in the case of progressive addition lenses, can be adjusted individually to the jointly determined accommodation and the vergence.

Following the first care, the proposed method and the presented apparatus can be used to monitor progress. If the jointly determined accommodation and vergence of a user change over time, it is possible to individually adjust the parameters of the optical devices, for example the addition power and/or the power of the inset in the case of progressive addition lenses, to the course of the myopia progression.

In a typical example, the assumption can be made that a myopic user with a refractive error of −3.0 dpt has an accommodation inaccuracy of 0.75 dpt, with an accuracy of the vergence of 4 Δdpt/dpt being able to be considered normal. A progressive addition lens specifically configured for the control of myopia is supplied to said user, with checkup measurements being carried out regularly within the scope of monitoring progress. The set addition power of the progressive addition lens reduces the inaccuracy of the accommodation to 0.25 dpt and can slow down an advance of myopia. After a period of 12 months, for example, it is established that the value of the inaccuracy of the accommodation once again corresponds to the value before the first care, whereupon the value of the addition power can be adjusted on an individual basis.

Hence, the present methods and apparatuses can particularly typically also be used for prediction values for development of refractive errors of the user.

The application of the proposed method and of the present apparatus as a screening tool and/or for monitoring progress within the scope of a control of myopia can be improved, as a matter of principle, by a presence of standard values, with the aid of which a user is able to make a decision as to whether, and in what form, an adjustment of the control of myopia is required. Until such standard values are available, the proposed method and the present apparatus can serve as a standardized examination method or examination equipment.

In respect of further configurations of the method for determining values for a control of myopia of the at least one eye of the user, reference is made to the description above or below relating to the method and apparatus for jointly determining the accommodation and the vergence of the at least one eye of the user.

As already mentioned, the method proposed here and the apparatus presented here for jointly determining accommodation and vergence of at least one eye of a user are suitable, in particular, for use in a method for producing a spectacle lens for the at least one eye of the relevant user. In accordance with the standard, sections 8.1.1 and 8.1.2, a "spectacle lens" is understood to mean an optical lens that is intended to serve for correcting refractive errors of the eye, the optical lens being worn in front of the user's eye, but not in contact with the eye. According to this further aspect of the present disclosure, the spectacle lens is produced by processing a lens blank or a semifinished spectacle lens product, wherein the lens blank or the semifinished spectacle lens product is processed on the basis of refraction data, wherein the refraction data take account of values for an accommodation and a vergence of the at least one eye of the user, the values being determined in accordance with the method described herein for jointly determining the accommodation and the vergence of the at least one eye of the user. In respect of further configurations of the method for producing a spectacle lens, reference is made to the description above or below relating to the method and apparatus for jointly determining the accommodation and the vergence of the at least one eye of the user. The refraction data typically comprise the dioptric power, specified as a result of the refraction determination, for correcting the visual acuity of the at least one eye of the user. Pursuant to the standard, section 9.3, the dioptric power is the general term for the focal power and the prismatic power of a spectacle lens.

The methods according to the disclosure and the proposed apparatus have numerous advantages over conventional apparatuses and methods. There can be, in a particularly advantageous manner, an objective joint determination of the accommodation and the vergence of the at least one eye of the user without specialist equipment, in particular without requiring subjective feedback from the user, for example in the form of a manual or acoustic input into the apparatus. Moreover, this does not require operation by specialist staff. Furthermore, the present methods and the proposed apparatus can be used as a screening tool for examining a possible risk in view of a development with regard to myopia and/or for monitoring the progress of already existing myopia, typically under the influence of additional optical devices, in particular progressive addition lenses.

In summary, in the context of the present disclosure, the exemplary embodiments described by the following clauses are particularly typical:

Clause 1. A method for jointly determining the accommodation and the vergence of at least one eye of a user, the method comprising the following steps:
a) presenting at least one symbol at at least one first distance in front of at least one eye of a user for stimulating the accommodation of the at least one eye;
b) capturing an eye movement of the at least one eye;
c) determining a refraction of the at least one eye with the accommodation of the at least one eye at the at least one first distance; and
d) jointly determining the accommodation and the vergence of the at least one eye by
determining a change in the refraction of the at least one eye with the accommodation of the at least one eye at the at least one first distance in relation to the accommodation of the at least one eye at a second distance; and
determining the vergence of the at least one eye from the eye movement of the at least one eye with the accommodation of the at least one eye at the at least one first distance.

Clause 2. The method as per the preceding clause, wherein the joint determination of the accommodation and the vergence is implemented, typically simultaneously, for both eyes of the user.

Clause 3. The method as per either of the preceding clauses, wherein a newly determined value for the refraction of the at least one eye with the accommodation of the at least one eye at the second distance is determined.

Clause 4. The method as per any one of the preceding clauses, wherein a known value for the refraction of the at least one eye with the accommodation of the at least one eye at the second distance is used.

Clause 5. The method as per any one of the preceding clauses, wherein at least one first distance or the second distance is selected for an accommodated state of the at least one eye.

Clause 6. The method as per the preceding clause, wherein the at least one first distance or the second distance for the accommodated state of the at least one eye is selected from at least one value from 15 cm to 60 cm, typically from 20 cm to 50 cm, in particular at approximately 20 cm, 25 cm, 40 cm and 50 cm.

Clause 7. The method as per any one of the preceding clauses, wherein at least one first distance or the second distance is selected for an unaccommodated state of the at least one eye.

Clause 8. The method as per the preceding clause, wherein the at least one first distance or second distance for an unaccommodated state of the at least one eye is selected from a value of at least 1 m, typically of at least 1.5 m, particularly typically of at least 2 m.

Clause 9. The method as per any one of the preceding clauses, wherein for determining the vergence of the at least one eye, an eye rotation of the at least one eye is captured during the accommodation of the at least one eye at the at least one first distance or at the second distance.

Clause 10. The method as per any one of the preceding clauses, wherein the refraction of the at least one eye is determined by means of a refraction measuring device, which is configured to capture the refraction of the at least one eye.

Clause 11. The method as per any one of the preceding clauses, wherein the refraction of the at least one eye is determined by capturing the eye movement of the at least one eye.

Clause 12. The method as per the preceding clause, wherein the eye movement of the at least one eye is captured on the basis of the symbol while a parameter of the symbol is altered, wherein a point in time is established, at which a recognition threshold of the user for the symbol arises from the eye movement.

Clause 13. The method as per the preceding clause, wherein the refraction of the at least one eye is determined from the parameter for the symbol established at the point in time.

Clause 14. The method as per one of the two preceding clauses, wherein the parameter of the presented symbol is altered.

Clause 15. The method as per the preceding clause, wherein the parameter of the at least one presented symbol is altered while the at least one presented symbol carries out a movement.

Clause 16. The method as per the preceding clause, wherein the movement of the at least one presented symbol is implemented continuously or in jumps.

Clause 17. The method as per any one of the five preceding clauses, wherein the presentation of the at least one symbol is repeated for different values of the parameter.

Clause 18. The method as per the preceding clause, wherein the presentation of the at least one symbol is repeated for different values of the parameter until the point in time is established.

Clause 19. The method as per any one of the seven preceding clauses, wherein the point in time is established by virtue of the eye movement metric of the user just still following or only just following the movement of the at least one presented symbol.

Clause 20. The method as per any one of the preceding clauses, wherein the eye movement of the at least one eye exhibits an eye movement metric.

Clause 21. The method as per the preceding clause, wherein the eye movement metric is selected from the group comprising eye movements of the eyes of the user; a pursuit eye movement; an eye movement relating to microsaccades; and an optokinetic nystagmus.

Clause 22. The method as per any one of the preceding clauses, wherein the presentation of the at least one symbol is implemented by virtue of the at least one symbol being arranged at the first distance in front of the eye.

Clause 23. The method as per any one of the preceding clauses, wherein the presentation of the at least one symbol is implemented by means of a visual display unit which is arranged at a fixed but selectable distance in front of the at least one eye of the user.

Clause 24. The method as per any one of the preceding clauses, wherein the presentation of the at least one symbol is implemented by virtue of the at least one symbol being projected at the first distance in front of the at least one eye.

Clause 25. The method as per any one of the preceding clauses, wherein the at least one symbol is projected onto the at least one eye in such a way that the user can recognize the at least one symbol virtually at a predetermined location in space, which corresponds to the first distance in front of the at least one eye of the user.

Clause 26. The method as per any one of the preceding clauses, wherein the at least one symbol is or comprises a periodic pattern.

Clause 27. The method as per the preceding clause, wherein a parameter of the presented pattern is or comprises at least one spatial frequency.

Clause 28. The method as per any one of the preceding clauses, wherein the at least one symbol is initially represented in a first direction and subsequently represented in a second direction which has been varied in relation to the first direction.

Clause 29. The method as per the preceding clause, wherein the vertex powers of each of the two principal meridians, which are perpendicular to one another, are successively determined for a spherocylindrical spectacle lens with astigmatic power.

Clause 30. The method as per any one of the preceding clauses, wherein the method is carried out while the user is wearing spectacles.

Clause 31. A method for determining values for a control of myopia of at least one eye of a user by means of a joint determination of accommodation and vergence of at least one eye of a user in accordance with a method as per any one of the preceding clauses, wherein the jointly determined accommodation and vergence of the at least one eye of the user are used as the values for the control of myopia.

Clause 32. A method for producing a spectacle lens for at least one eye of a user, wherein the spectacle lens is produced by processing a lens blank or a semifinished spectacle lens product, wherein the lens blank or the semi-finished spectacle lens product is processed on the basis of refraction data, wherein the refraction data take account of values for an accommodation and a vergence of the at least one eye of the user, which were obtained in accordance with a method as per any one of the preceding clauses.

Clause 33. A computer program, comprising executable instructions for carrying out a method as per any one of the preceding clauses.

Clause 34. An apparatus for jointly determining the accommodation and the vergence of at least one eye of a user, the apparatus comprising:
a) a device configured to present at least one symbol at at least one first distance in front of at least one eye of a user for stimulating the accommodation of the at least one eye;
b) an eye movement measuring device configured to capture an eye movement of the at least one eye; and
c) an evaluation unit configured to jointly determine the accommodation, from the change in the refraction, and the vergence, from the eye movement, in accordance with a method as per any one of the preceding clauses.

Clause 35. The apparatus as per the preceding clause, wherein the evaluation unit is configured to jointly determine the accommodation and the vergence in accordance with a method as per any one of the preceding clauses relating to a method.

Clause 36. The apparatus as per either of the two preceding clauses, wherein the eye movement measuring device has a light source for illuminating the eye and a camera for capturing the eye movement.

Clause 37. The apparatus as per the preceding clause, wherein the light source is configured to emit in the infrared spectral range and the camera has a sensitivity in the infrared spectral range.

Clause 38. The apparatus as per any one of the four preceding clauses, further comprising a refraction measuring device configured to capture the refraction of the at least one eye.

Clause 39. The apparatus as per any one of the five preceding clauses, further comprising a visual display unit configured to present the symbol at the first distance in front of the at least one eye.

Clause 40. The apparatus as per any one of the six preceding clauses, further comprising a projection device, the latter being configured to image the symbol on the at least one eye of the user.

Clause 41. A data processing apparatus, comprising:
a) means for presenting at least one symbol at at least one first distance in front of at least one eye of a user for stimulating the accommodation of the at least one eye;
b) means for capturing at least one eye movement of the at least one eye; and c) means for determining a refraction of the at least one eye with the accommodation of the at least one eye at the at least one first distance;
d) jointly determining the accommodation and the vergence of the at least one eye by
    determining a change in the refraction of the at least one eye with the accommodation of the at least one eye at the at least one first distance in relation to the accommodation of the at least one eye at at least one second distance; and
    determining the vergence of the at least one eye from the at least one eye movement of the at least one eye with the accommodation of the at least one eye at the at least one first distance.

Clause 42. An apparatus for determining an accommodation of at least one eye of a user, wherein the apparatus comprises:
a) a device configured to present at least one symbol at at least one first distance in front of at least one eye of a user for stimulating the accommodation of the at least one eye;
b) an eye movement measuring device configured to capture an eye movement of the at least one eye; and
c) an evaluation unit,
    i) wherein the evaluation unit is configured to determine the accommodation from the change in the refraction by way of
    determining a change in the refraction of the at least one eye with the accommodation of the at least one eye at the at least one first distance in relation to the accommodation of the at least one eye at a second distance.

Clause 43. A computer-implemented method for jointly determining accommodation and vergence of at least one eye of a user, the method comprising the following steps:
a) presenting at least one symbol at at least one first distance (166) in front of at least one eye of a user for stimulating the accommodation of the at least one eye;
b) capturing an eye movement of the at least one eye; and
c) determining a refraction of the at least one eye with the accommodation of the at least one eye at the at least one first distance;
d) jointly determining the accommodation and the vergence of the at least one eye by
    determining a change in the refraction of the at least one eye with the accommodation of the at least one eye at the at least one first distance in relation to the accommodation of the at least one eye at a second distance; and
    determining the vergence of the at least one eye from the eye movement of the at least one eye with the accommodation of the at least one eye at the at least one first distance.

Clause 44. The computer-implemented method as per the preceding clause, characterized in that the joint determination of the accommodation and the vergence is implemented for both eyes of the user.

Clause 45. The computer-implemented method as per either of clauses 43 and 44, characterized in that a newly determined value for the refraction of the at least one eye with the accommodation of the at least one eye at the second distance is determined or in that a known value for the refraction of the at least one eye with the accommodation of the at least one eye at the second distance is used.

Clause 46. The computer-implemented method as per any one of clauses 43 to 45, characterized in that the at least one first distance is chosen for an accommodated state of the at least one eye and the second distance is chosen for an unaccommodated state of the at least one eye, or in that the at least one first distance is chosen for an unaccommodated state of the at least one eye and the second distance is chosen for an accommodated state of the at least one eye.

Clause 47. The computer-implemented method as per any one of clauses 43 to 46, characterized in that for the purposes of determining the vergence of the at least one eye, an eye rotation of the at least one eye is captured while the at least one eye is accommodated at the at least one first distance.

Clause 48. The computer-implemented method as per any one of clauses 43 to 47, characterized in that the refraction of the at least one eye is determined by means of a refraction measuring device, which is configured to capture the refraction of the at least one eye.

Clause 49. The computer-implemented method as per any one of clauses 43 to 48, characterized in that the refraction of the at least one eye is determined by capturing the eye movement of the at least one eye on the basis of the at least one symbol while a parameter of the at least one symbol is altered, wherein a point in time is determined at which a recognition threshold of the user for the at least one symbol emerges from the eye movement, wherein the refraction of the at least one eye is determined from the parameter for the at least one symbol defined at this point in time.

Clause 50. The computer-implemented method as per any one of clauses 43 to 49, characterized in that the eye movement of the at least one eye has an eye movement metric, wherein the eye movement metric is selected from the group comprising a pursuit eye movement, an eye movement relating to microsaccades, and an optokinetic nystagmus.

Clause 51. The computer-implemented method as per any one of clauses 43 to 50, characterized in that the at least one symbol is presented by virtue of
a) the at least one symbol being arranged at the first distance in front of the at least one eye;
b) the at least one symbol being projected at the first distance in front of the at least one eye; and/or
c) the at least one symbol being projected onto the at least one eye such that the user can virtually recognize the at least one symbol at the first distance in front of the at least one eye.

Further details and features of the disclosure will become apparent from the following description of typical exemplary embodiments. In this case, the respective features can be realized by themselves or as a plurality in combination with one another. The disclosure is not restricted to the exemplary embodiments. The exemplary embodiments are illustrated schematically in the drawings. Identical reference numerals in the individual figures denote identical or functionally identical elements or elements corresponding to one another with regard to their functions.

BRIEF DESCRIPTION OF THE DRAWINGS

The disclosure will now be described with reference to the drawings wherein.

DESCRIPTION OF EXEMPLARY EMBODIMENTS

Figure 1:
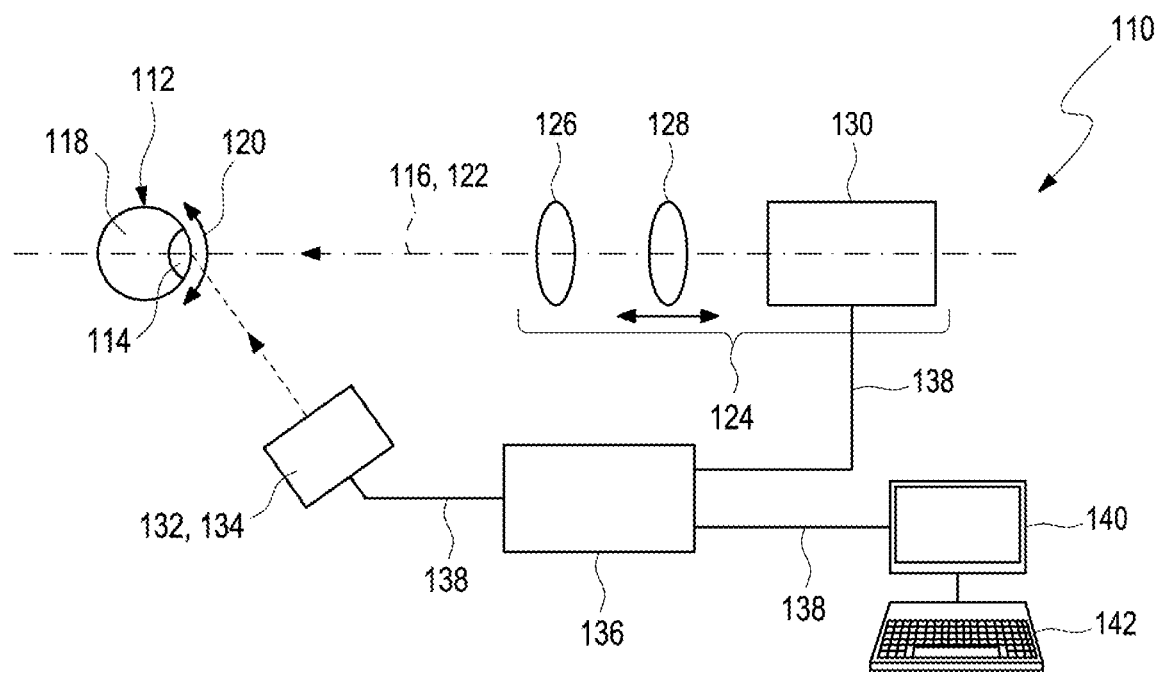
FIG. 1 shows a typical exemplary embodiment of an apparatus according to the disclosure for jointly determining accommodation and vergence of at least one eye of a user.

FIG. 1 shows a schematic illustration of a typical exemplary embodiment of an apparatus 110 according to the disclosure for jointly determining accommodation and vergence of one or both eyes 112, 112' of a user. In this case, FIG. 1 schematically illustrates only a single eye 112 of the user, the eye 112 having a pupil 114 through which a light beam 116 enters an interior 118 of the eye 112. In this case, there is a change in the direction of the light, referred to as "refraction," in the eye 112 of the user. Furthermore, the eye 112 can carry out an eye rotation 120. As illustrated in more detail in FIG. 3, opposing eye movements of the two eyes 112, 112' of a pair of eyes of the user, wherein each of the two eyes 112, 112' carries out an eye rotation 120 in a respectively opposite direction of rotation about mutually parallel axes 122, are referred to as "vergence."

The proposed apparatus 110 comprises a device 124 for presenting a symbol at at least one desired distance in front of the eye 112 of the user, wherein the symbol (not illustrated) is suitable for stimulating the accommodation of the eye 112. In this case, the symbol comprises an optotype, selected from one or more letters, numerals, signs, images or patterns, which can be presented in color or black and white. The symbol can be presented in monocular fashion, that is to say separately for each eye 112, or in binocular fashion, that is to say together and simultaneously for both eyes 112, 112' of a pair of eyes. In this case, as illustrated schematically in FIG. 1, the device 124 may comprise an optional fixed lens 126, a movable lens 128 and a visual display unit 130. However, a different embodiment of the device 124 is possible.

In the embodiment as per FIG. 1, the symbol is projected onto the eye 112 by means of the device 124, as illustrated in FIG. 1, such that the user can virtually recognize the symbol at the predetermined location in space, which corresponds to the desired distance in front of the eye 112 of the user. In an alternative embodiment (not illustrated), the apparatus 110 may comprise a projection device configured to project the symbol at the predetermined location in space, which corresponds to the desired distance in front of the eye 112 of the user. In a further alternative embodiment (not illustrated), the device 124 may comprise a visual display unit arranged at the desired distance in front of the eye 112 of the user. In this case, the visual display unit can be selected from a monitor, a screen or a display, wherein the visual display unit can be configured to be looked at or, typically, looked through. However, further embodiments of the device 124 are conceivable.

Furthermore, the device 124 for presenting the symbol of the user can be configured to alter a parameter of the symbol, wherein the parameter relates to a property of the symbol, selected, depending on the symbol, from an extent, orientation, frequency, contrast or color, including black and white, of the symbol or a part thereof. In the case of a periodic pattern, the parameter may relate to a repeatedly presented structure, in particular to an arrangement of periodic maxima or minima, in particular to at least one spatial frequency of the periodic pattern. Furthermore, the device 124 for presenting the symbol can be configured to implement a movement of the symbol, in particular in continuous fashion or in jumps, wherein the parameter of the presented symbol is typically altered while the presented symbol carries out the movement. It is irrelevant in this context if the symbol only carries out an apparent movement.

The proposed apparatus 110 further comprises an eye movement measuring device 132, which is configured to capture an eye movement of the eye 112 and which is therefore also referred to as an "eyetracker." The eye movement measuring device 132 can typically comprise a camera 134, particularly typically a video camera, in particular in order to be able to carry out video-based "eye tracking" by virtue of recording image sequences of an eye area of the user and evaluating these by means of image processing in order to establish at least one eye movement metric therefrom. To this end, known algorithms in particular can be used in each case. In this case, the eye movement metric relates to a measure linked to the movement of the eye 112 of the user, wherein the movement of the eye 112 of the user is caused by the symbol, which acts as a stimulus. The eye movement metric can be selected from: opposing eye movements of the two eyes 112, 112' of the user; a pursuit eye movement; an eye movement relating to microsaccades, comprising a microsaccade direction, microsaccade rate or a saccade accuracy; or an optokinetic nystagmus. However, further types of eye movement metrics, for example a fixation duration, are possible. A selection of the eye movement metrics substantially depends on an accuracy of the eye movement measuring device 132 and the respective use purpose. While opposing eye movements can be used in particular for determining the vergence, pursuit eye movements can typically be suitable for determining the refraction.

Moreover, geometric data relating to the eye 112, typically the pupil 114, in particular position and diameter of the pupil 114, can be determined from the recorded image sequences by means of image processing and the line of sight of the eye 112, for example, can be determined therefrom. To this end, it is possible to use methods which include selected reflection points that may arise on the front side and/or back side of the cornea and lens if the eye 112 is irradiated by a light source. In particular, it is possible to record a corneal reflection or any other reflection. Since the corneal reflection does not move without a head movement, but the pupil 114 changes its position during the eye movement, the eye rotation 120 can be deduced therefrom. According to the disclosure, the capturing of the eye movement, in particular the eye rotation 120, serves to determine the vergence by virtue of capturing and evaluating the opposing eye movements of the two eyes 112, 112' of the user, wherein each of the two eyes 112, 112' carries out an eye rotation 120 in an opposite direction of rotation about mutually parallel axes 122, 122'.

As disclosed in EP 3730037, the eye movement of the eye 112 of the user can be capture on the basis of the symbol while at least one parameter of the symbol is altered. To this end, data for capturing the eye movement of the user which were recorded by the camera 134 can be used to determine the line of sight of the user to the presented symbol. In the case of an increasing reduction in one of the parameters of the symbol, in particular in the spatial frequency in the periodic pattern, the pursuit eye movement of the user will correspond to the movement of the symbol for as long as the user can recognize the presented symbol. Once a point in time has been reached at which the user just can no longer recognize the presented symbol, in particular the periodic pattern, and said symbol can consequently no longer act as a stimulus for the eye 112 of the user, the pursuit eye movement of the user will deviate from the movement of the symbol. Conversely, if the point in time is reached at which the user for the first time can just recognize the presented symbol, in particular the periodic pattern, and said symbol consequently for the first time acts as a stimulus for the eye 112 of the user, the pursuit eye movement of the user starts to follow the movement of the symbol. Independently of the type of configuration it is preferable in this context to set a threshold by means of which a degree of deviation of the pursuit eye movement of the user from the movement of the symbol is established as the sought-after point in time. The point in time at which the deviation exceeds or drops below the defined threshold in this case represents the sought-after point in time. A value for the refraction of the eye 112 of the user can be determined from the value of the parameter used at the established point in time to set the parameter of the symbol, this being implemented from the establishment of the point in time. Alternatively, a power vector can be specified for this purpose.

The proposed apparatus 110 furthermore comprises an evaluation unit 136, which is configured to jointly determine the accommodation, from the change in refraction, and the vergence, from the eye movement. In this case, a wired or wireless connection 138 can be provided between the eye movement measuring device 132 and the evaluation unit 136. There may be a further connection 138 between the evaluation unit 136 and the device 124 for presenting the symbol. In this way, the evaluation unit 136 can also be used to control the eye movement measuring device 132 and the device 124 for presenting the symbol, in particular in order to set the parameter of the symbol. Furthermore, results from the joint determination of the accommodation and the vergence can be made available to the user or any other person, in particular an optician or ophthalmologist, for example by means of a monitor 140. Furthermore, a keyboard 142 may be provided for the input of values for the aforementioned control. However, further types of the implementation of the evaluation unit 136 are possible.

According to the disclosure, the evaluation unit 136 is configured to jointly determine the accommodation, from the change in the refraction, and the vergence, from the eye movement. To this end, data from capturing the eye movement of the user, recorded by the eye movement measuring device 132, are transmitted to the evaluation unit 136. Furthermore, the parameters of the symbol 122 are known on account of the electronic control of the device 124 and can therefore be used by the evaluation unit 136 for the desired evaluation. Further details regarding the determination of the accommodation and the vergence can be found below in the description relating to FIG. 3.

Figure 2:
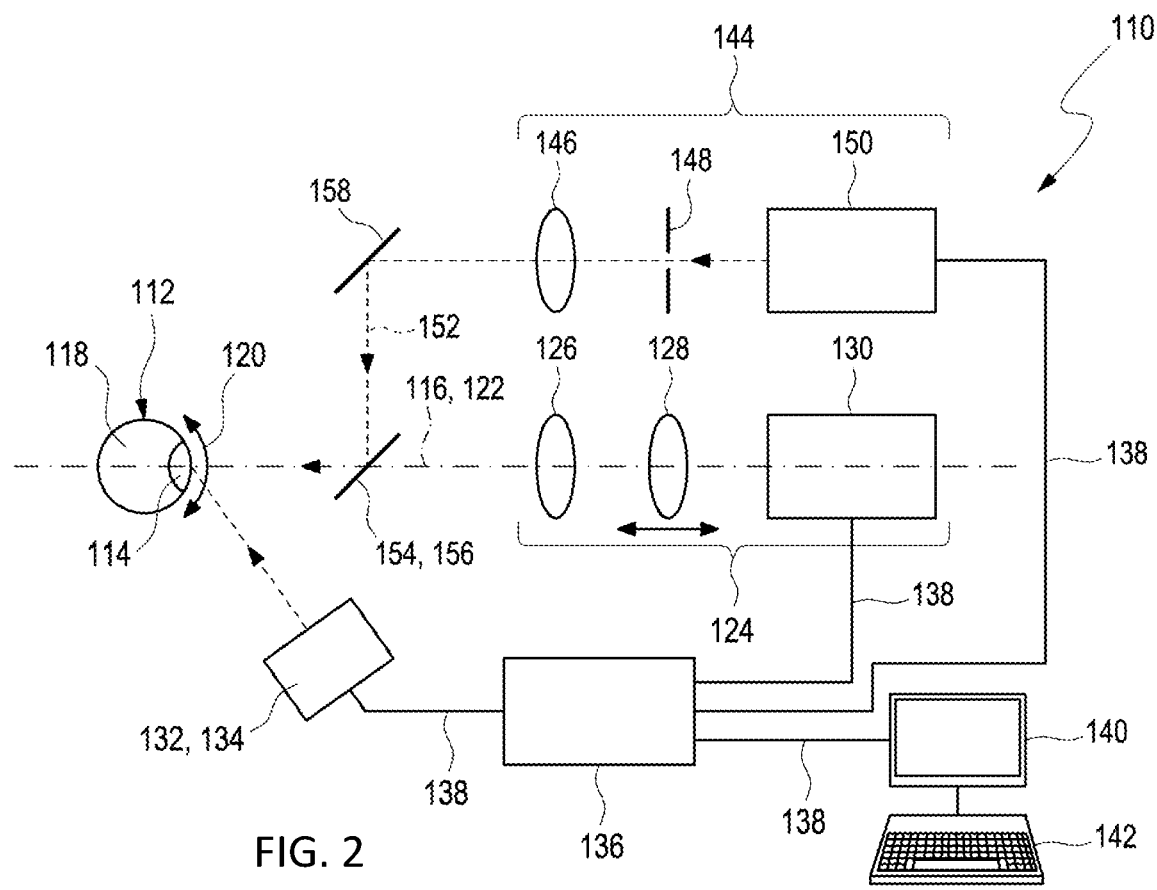
FIG. 2 shows a particularly typical exemplary embodiment of the apparatus according to the disclosure for jointly determining accommodation and vergence of the at least one eye of the user.

FIG. 2 shows a schematic illustration of a particularly typical exemplary embodiment of the apparatus 110 according to the disclosure for jointly determining the accommodation and the vergence of eyes 112, 112' of a user. As illustrated in FIG. 2, the refraction of the eye can be particularly typically determined using a refraction measuring device 144 configured to capture the refraction of the eye 112, wherein the refraction measuring device 144 can be controlled, in particular, using the evaluation unit 136. In this case, the refraction measuring device 144 may comprise a lens 146, a stop 148 and an optical sensor 150, which are configured to determine the defocusing of the eye 112 of the user. However, other ways of configuring the refraction measuring device 144 are possible. To impinge the refraction measuring device 144 with part of the light beam 152 that is reflected by the eye 112, additional provision can be made for a beam splitter 154, in particular a partly transparent mirror 156, and a non-transparent deflection mirror 158, as shown schematically in FIG. 2. However, other or further optical elements are conceivable for this purpose. Regarding further details of the apparatus 110 presented in FIG. 2, reference is made to the above description of the apparatus 110 as per FIG. 1.

In a further typical configuration, the apparatus 110 according to FIG. 1 or 2 may comprise two separate devices 124 for presenting a symbol, two separate eye movement measuring devices 132 and, moreover in FIG. 2, two separate refraction measuring devices 144, which may be configured for the simultaneous, joint determination of the accommodation and the vergence of the two eyes 112, 112' of the user.

Figure 3:
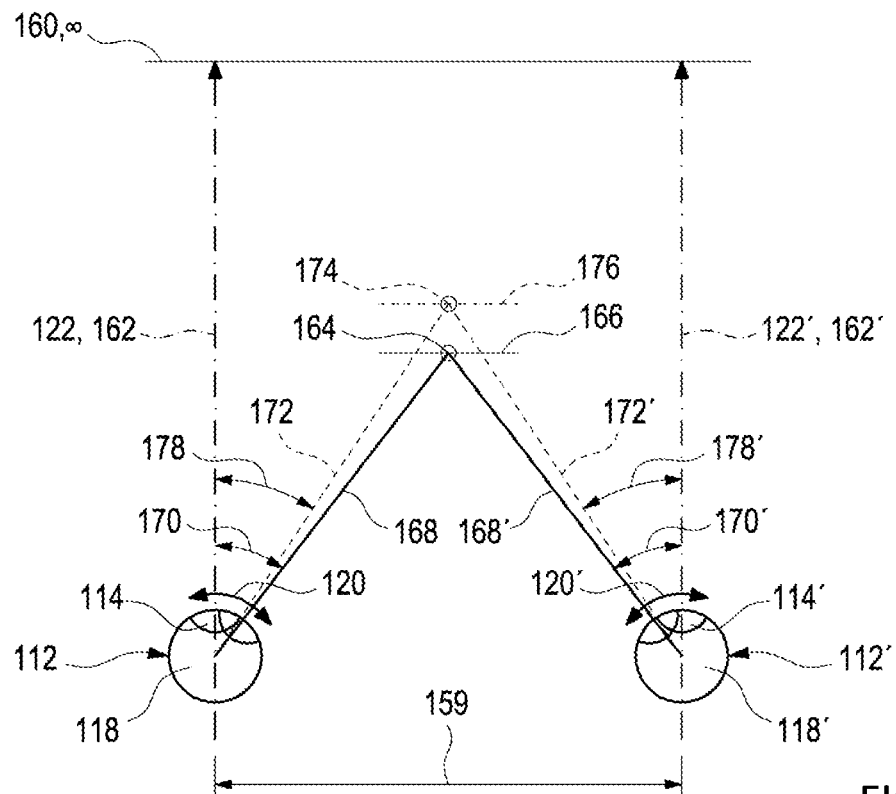
FIG. 3 shows a schematic illustration of the functionality of the method according to the disclosure for jointly determining the accommodation and the vergence of the at least one eye of the user.

FIG. 3 shows a schematic illustration of the functionality of the method according to the disclosure for jointly determining the accommodation and the vergence of the eyes 112, 112' of the user, which are spaced apart by an interpupillary distance 159 (abbreviated "IPD") and which each have a pupil 114, 114'. In this illustration, the two eyes 112, 112' of the user initially each fixate a target at a second distance 160, which is at infinity ∞ in this case. In this case, the line of sight 162, 162' of each eye 112, 112' is aligned along a respective axis 122, 122', with the axes being parallel to one another. Another value for the second distance 160 is possible, however, for example a value of at least 1 m, typically at least 1.5 m, particularly typically at least 2 m, at which the eye 112 adopts a substantially unaccommodated state.

In the further illustration as per FIG. 3, the two eyes 112, 112' of the user should subsequently fixate a target 164 at a first distance 166 in order to be able to image the symbol situated at the target 164 as sharply as possible onto the retinal plane of the eye. Typically, at least two, typically at least three, at least four, at least five or at least six values for the first distance 166 can be used to this end, wherein values from 15 cm to 60 cm, particularly typically from 20 cm to 50 cm, in particular at approximately 20 cm, 25 cm, 40 cm and 50 cm are typically selected, at which an accommodated state of the eye is present. A value of 40 cm for the first distance 160 is slated for the exemplary embodiment presented here in exemplary fashion; however, other values are possible. By choosing two or more different first distances 166, it is advantageously possible to obtain a measurement curve from which an evaluation with an increased accuracy is facilitated, in particular by determining a gradient of the measurement curve.

In the case where the two eyes 112, 112' do not have a refractive error, the two eyes 112, 112' would adopt altered lines of sight 168, 168' (solid lines) in order to fixate at the target 164 at the first distance 166, as shown schematically in FIG. 3. In the case of the value of 40 cm slated here for the first distance 160 in exemplary fashion, this corresponds to an accommodation of 2.5 dpt. Such a change in the lines of sight 162, 162' to the altered lines of sight 168, 168' would correspond to a convergence need 170, 170' of the two eyes 112, 112' through the angle specified in FIG. 3, which is referred to as "vergence." To this end, the two eyes 112, 112' would have to carry out the opposing eye rotations 120, 120', in each case in an opposing direction of rotation, through the specified angle about the mutually parallel axes 122, 122'.

As already mentioned above, a corneal reflection of each pupil 114, 114' of the two eyes 112, 112' can be recorded for the purposes of determining the vergence. This is in particular advantageous as a result of the fact that the respective corneal reflection does not move without a head movement, but the pupils 114, 114' change their respective position during the eye movement such that the associated eye rotation 120, 120' can be reliably deduced therefrom. However, other ways of determining the vergence of the two eyes 112, 112' are possible.

However, if the two eyes 112, 112' each have a refractive error, the two eyes 112, 112' would each adopt differently altered lines of sight 172, 172' (dashed lines), as illustrated schematically in FIG. 3. By way of example, if the accommodation were only 2.3 dpt instead of 2.5 dpt, an accommodation error of 0.2 dpt would be present in this case. As a result, the target 164 situated at the first distance 166 would appear to be situated at a different location 174 at an apparent first distance 176. The change in the lines of sight 162, 162' to the differently altered lines of sight 172, 172' caused thereby would correspond to a different convergence need 178, 178' of the two eyes 112, 112' through the angle likewise specified in FIG. 3.

In order nevertheless to be able to fixate the target 164 at the correct first distance 166, the user consequently requires in each case a correction of the refraction of the two eyes 112, 112' by a value of 0.2 dpt, taking account of the corresponding vergence of the two eyes 112, 112' during the intended fixation of the two eyes 112, 112' at the target 164 at the first distance 166. Hence, the joint determination 220 of the accommodation and the vergence of the eyes 112, 112', desired here, can be implemented by determining the change in the refraction of the eyes 112, 112' with the accommodation at the first distance 166 in relation to the accommodation at the second distance 160, which corresponds here to a value of 0.2 dpt in exemplary fashion. Hence, it is possible in particular to determine a value for the absolute value of the vergence AC which is set for a certain accommodation distance A (AC/A).

Figure 4:
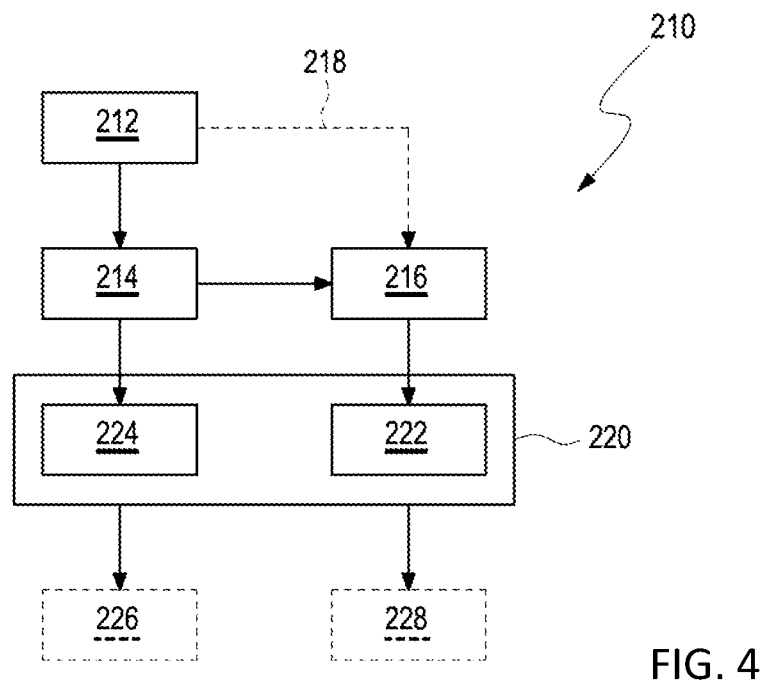
FIG. 4 shows a typical exemplary embodiment of the method according to the disclosure for jointly determining the accommodation and the vergence of the at least one eye of the user.

FIG. 4 schematically shows a flowchart of a typical exemplary embodiment of a method 210 according to the disclosure for jointly determining the accommodation and the vergence of the eyes of the user.

According to step a) there initially is in this case a presentation 212 of the symbol at at least one first distance in front of the eye 112 of the user for stimulating the accommodation of the eye 112. To this end, use can be made in particular of the device 124 for presenting a symbol, which is suitable for stimulating the accommodation of the eye 112, at the at least one desired distance in front of the eye 112 of the user.

According to step b) there is, typically adjoining this, a capturing 214 of the eye movement of the eye 112 of the user on the basis of the presented symbol. To this end, use can be made in particular of the eye movement measuring device 132, which is configured to capture an eye movement of the eye 112 and which may therefore typically comprise a camera 134, particularly typically a video camera. According to the disclosure, the capturing of an eye movement serves to determine the sought-after vergence by virtue of capturing and evaluating opposing eye movements of the two eyes 212 of a pair of eyes of the user, wherein each of the two eyes 112 carries out an eye rotation 120 in a respectively opposite direction of rotation about mutually parallel axes 122.

According to step c) there is a determination 216 of the refraction of the eye 112 with the accommodation of the eye 112 at the at least one first distance. In a typical configuration of the present disclosure, the implemented capturing 214 of the eye movement of the eye 112 of the user can additionally also be used to determine 216 the refraction of the eye 112, for the purposes of which, for example, use can be made of the method disclosed in EP 3730037 A1. Alternatively or in addition, a measurement 218 of the refraction of the eye 112 can be undertaken by means of the above-described refraction measuring device 144, which is configured to capture the refraction of the eye 112 with the accommodation of the eye 112 at the symbol which acts on the eye 112 as a stimulus.

Finally, as per step d) there is the joint determination 220 of the accommodation and the vergence of the eye 112 of the user by determining 222 a change in the refraction of the eye 112 with the accommodation of the eye 112 at the at least one first distance in relation to the accommodation of the eye 112 at a second distance and by determining 224 the vergence of the eye 112 from the eye movement of the eye 112, in particular in the case of the eye rotation 120 of each of the two eyes 112 about mutually parallel axes 122, in each case in an opposite direction of rotation, with the accommodation of the eye 112 at the at least one first distance.

In a special embodiment, which can typically be used when monitoring the progress of the two eyes 112, 112' of the user over a period of time, for example over one or more weeks, months, quarters or years, it is possible to dispense with the current determination 218, in particular current measurement 218, of the refraction with the accommodation of the eyes 112, 112' at the second distance 160 and instead use a known value for the refraction with the accommodation at the second distance 160, typically from an earlier determination 216 of this value.

The values for the accommodation and the vergence of the eyes 112, 112' of the user, obtained by means of the method 210, can typically be used as a prediction value 226 relating to the development of refractive errors by the user.

Likewise, these values can be considered when determining refraction data 228 used to process a lens blank or semifinished spectacle lens product in a method for producing spectacle lenses for the eyes 112, 112' of the user. From this, it is possible in particular to determine a spherocylindrical lens from the determination of the refraction and the vergence, which spherocylindrical lens can be used as a spectacle lens in order to compensate refractive errors occurring as a consequence of the defocusing of the eyes 112, 112', in such a way that the best possible optimal image quality can be obtained for the user.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

110 Apparatus
112, 112' Eye
114, 114' Pupil
116 Light beam
118 Interior
120, 120' Eye rotation
122, 122' Axis
124 Device for presenting a symbol
126 Fixed lens
128 Moveable lens
130 Visual display unit
132 Eye movement measuring device (eyetracker)
134 (Video) camera
136 Evaluation unit
138 Connection
140 Monitor 142 Keyboard
144 Refraction measuring device
146 Lens
148 Stop
150 Optical sensor
152 Reflected light beam
154 Beam splitter
156 Partly transparent mirror
158 Deflection mirror
159 Interpupillary distance
160 Second distance
162, 162' Line of sight
164 Target
166 First distance
168, 168' Altered line of sight
170, 170' Convergence need
172, 172' Differently altered line of sight
174 Different location
176 Apparent first distance
178, 178' Different convergence need
210 Method
212 Presentation of the symbol
214 Capturing of the eye movement
216 Determination of the refraction
218 Measurement of the refraction
220 Joint determination of the accommodation and the vergence
222 Determining a change in the refraction
224 Determining the vergence
226 Prediction value
228 Refraction data

The invention claimed is:

1. A method for jointly determining accommodation and vergence of at least one eye of a user, the method comprising the following steps:
   a) presenting at least one symbol at at least one first distance in front of at least one eye of a user to stimulate an accommodation of the at least one eye;
   b) capturing at least one eye movement of the at least one eye;
   c) determining a refraction of the at least one eye with the accommodation of the at least one eye at the at least one first distance; and
   d) jointly determining the accommodation and the vergence of the at least one eye by:
      determining a change in the refraction of the at least one eye with the accommodation of the at least one eye at the at least one first distance in relation to the accommodation of the at least one eye at at least one second distance; and
      determining the vergence of the at least one eye from the at least one eye movement of the at least one eye with the accommodation of the at least one eye at the at least one first distance,
      wherein the refraction of the at least one eye is determined by capturing the at least one eye movement of the at least one eye based on the at least one symbol while a parameter of the at least one symbol is altered, wherein a point in time is determined at which a recognition threshold of the user for the at least one symbol emerges from the at least one eye movement, and wherein the refraction of the at least one eye is determined from the parameter for the at least one symbol defined at the point in time.

2. The method as claimed in claim 1, wherein the joint determination of the accommodation and the vergence is implemented for both eyes of the user.

3. The method as claimed in claim 1, wherein a newly determined value for the refraction of the at least one eye with the accommodation of the at least one eye at the at least one second distance is determined or wherein a known value for the refraction of the at least one eye with the accommodation of the at least one eye at the at least one second distance is used.

4. The method as claimed in claim 1, wherein the refraction of the at least one eye is determined with a refraction measuring device, which is configured to capture the refraction of the at least one eye.

5. The method as claimed in claim 1, wherein the eye movement of the at least one eye has an eye movement metric, wherein the eye movement metric is selected from the group consisting of a pursuit eye movement, an eye movement relating to microsaccades, and an optokinetic nystagmus.

6. The method as claimed in claim 1, wherein the at least one symbol is presented by virtue of:
   the at least one symbol being arranged at the first distance in front of the at least one eye;
   the at least one symbol being projected at the first distance in front of the at least one eye; and/or
   the at least one symbol being projected onto the at least one eye such that the user can virtually recognize the at least one symbol at the first distance in front of the at least one eye.

7. The method as claimed in claim 1, wherein the at least one first distance is selected for an accommodated state of the at least one eye and the at least one second distance is selected for an unaccommodated state of the at least one eye, or wherein the at least one first distance is selected for an unaccommodated state of the at least one eye and the at least one second distance is selected for an accommodated state of the at least one eye.

8. The method as claimed in claim 1, wherein for purposes of determining the vergence of the at least one eye, an eye rotation of the at least one eye is captured while the at least one eye is accommodated at the at least one first distance.

9. A computer program comprising executable instructions for carrying out a method for jointly determining accommodation and vergence of at least one eye of a user, the method comprising the following steps:
   a) presenting at least one symbol at at least one first distance in front of at least one eye of a user for stimulating the accommodation of the at least one eye;
   b) capturing at least one eye movement of the at least one eye; and
   c) determining a refraction of the at least one eye with the accommodation of the at least one eye at the at least one first distance;
   d) jointly determining the accommodation and the vergence of the at least one eye by:
      determining a change in the refraction of the at least one eye with the accommodation of the at least one eye at the at least one first distance in relation to the accommodation of the at least one eye at at least one second distance; and
      determining the vergence of the at least one eye from the at least one eye movement of the at least one eye with the accommodation of the at least one eye at the at least one first distance,
   wherein the refraction of the at least one eye is determined by capturing the at least one eye movement of the at least one eye based on the at least one symbol while a parameter of the at least one symbol is altered, wherein a point in time is determined at which a recognition threshold of the user for the at least one symbol emerges from the at least one eye movement, wherein the refraction of the at least one eye is determined from the parameter for the at least one symbol defined at the point in time.

10. A computer-readable non-transitory data medium, on which the computer program as claimed in claim 9 is stored.

11. A computer-readable non-transitory storage medium comprising instructions that, upon execution by a computer, cause the latter to carry out the steps of a method for producing a spectacle lens for at least one eye of a user, wherein the spectacle lens is produced by processing a lens blank or a semi-finished spectacle lens product, wherein the lens blank or the semi-finished spectacle lens product is processed based on refraction data, wherein the refraction data take into account values for an accommodation and a vergence of at least one eye of the user, wherein a method for jointly determining the accommodation and the vergence of the eye of the user is used, the method for producing the spectacle lens comprising the following steps:
   a) presenting at least one symbol at at least one first distance in front of at least one eye of a user for stimulating the accommodation of the at least one eye;
   b) capturing at least one eye movement of the at least one eye; and
   c) determining a refraction of the at least one eye with the accommodation of the at least one eye at the at least one first distance;
   d) jointly determining the accommodation and the vergence of the at least one eye by:
      determining a change in the refraction of the at least one eye with the accommodation of the at least one eye at the at least one first distance in relation to the accommodation of the at least one eye at at least one second distance; and
      determining the vergence of the at least one eye from the at least one eye movement of the at least one eye with the accommodation of the at least one eye at the at least one first distance,
   wherein the refraction of the at least one eye is determined by capturing the at least one eye movement of the at least one eye on the basis of the at least one symbol while a parameter of the at least one symbol is altered, wherein a point in time is determined at which a recognition threshold of the user for the at least one symbol emerges from the at least one eye movement, wherein the refraction of the at least one eye is determined from the parameter for the at least one symbol defined at the point in time.

12. An apparatus for jointly determining accommodation and vergence of at least one eye of a user, the apparatus comprising:
   a device configured to present at least one symbol at at least one first distance in front of at least one eye of a user for stimulating the accommodation of the at least one eye;
   an eye movement measuring device configured to capture at least one eye movement of the at least one eye; and
   an evaluation unit configured to jointly determine the accommodation, from the change in the refraction, and the vergence, from the eye movement, by:
      determining a change in the refraction of the at least one eye with the accommodation of the at least one eye at the at least one first distance in relation to the accommodation of the at least one eye at at least one second distance; and
      determining the vergence of the at least one eye from the at least one eye movement of the at least one eye with the accommodation of the at least one eye at the at least one first distance,
   wherein the evaluation unit is further configured to carry out the ascertainment of the refraction of the at least one eye by capturing the at least one eye movement of the at least one eye based on the at least one symbol while a parameter of the at least one symbol is altered, wherein a point in time is determined at which a recognition threshold of the user for the at least one symbol emerges from the at least one eye movement, and wherein the refraction of the at least one eye is determined from the parameter for the at least one symbol defined at the point in time.

13. The apparatus as claimed in claim 12, wherein the eye movement measuring device comprises a light source for illuminating the at least one eye and a camera for capturing the eye movement.

14. The apparatus as claimed in claim 12, wherein the apparatus further comprises at least one of the following devices:
   a refraction measuring device configured to capture the refraction of the at least one eye;
   a monitor configured to present the at least one symbol at the first distance in front of the at least one eye; and/or
   a projection device configured to image the at least one symbol on the at least one eye of the user.

15. A data processing apparatus, comprising:
   a) means for presenting at least one symbol at at least one first distance in front of at least one eye of a user for stimulating the accommodation of the at least one eye;
   b) means for capturing at least one eye movement of the at least one eye; and
   c) means for determining a refraction of the at least one eye with the accommodation of the at least one eye at the at least one first distance; and
   d) jointly determining the accommodation and the vergence of the at least one eye by:
      determining a change in the refraction of the at least one eye with the accommodation of the at least one eye at the at least one first distance in relation to the accommodation of the at least one eye at at least one second distance; and
      determining the vergence of the at least one eye from the at least one eye movement of the at least one eye with the accommodation of the at least one eye at the at least one first distance,
   wherein the refraction of the at least one eye is determined by capturing the at least one eye movement of the at least one eye based on the at least one symbol while a parameter of the at least one symbol is altered, wherein a point in time is determined at which a recognition threshold of the user for the at least one symbol emerges from the at least one eye movement, and wherein the refraction of the at least one eye is determined from the parameter for the at least one symbol defined at this point in time.

16. A computer program comprising instructions that, upon execution of the program by a computer, cause the latter to carry out a method comprising the following steps:
   a) presenting at least one symbol at at least one first distance in front of at least one eye of a user for stimulating the accommodation of the at least one eye;
   b) capturing at least one eye movement of the at least one eye;
   c) determining a refraction of the at least one eye with the accommodation of the at least one eye at the at least one first distance;

d) jointly determining the accommodation and the vergence of the at least one eye by:
   determining a change in the refraction of the at least one eye with the accommodation of the at least one eye at the at least one first distance in relation to the accommodation of the at least one eye at at least one second distance;
   determining the vergence of the at least one eye from the at least one eye movement of the at least one eye with the accommodation of the at least one eye at the at least one first distance; and
e) determining a change of myopia of the at least one eye of the user from a ratio of the vergence of the at least one eye to the change in the accommodation from the change in the refraction of the at least one eye with the accommodation of the at least one eye at the at least one first distance in relation to the accommodation of the at least one eye at the at least one second distance.

17. A computer-readable non-transitory data storage medium, on which the computer program as claimed in claim 16 is stored.

18. A computer program comprising instructions that, upon execution of the program by a computer, cause the latter to carry out a method for determining values for a control of myopia of at least one eye of a user with a method for jointly determining accommodation and vergence of at least one eye of a user, the method comprising the following steps:
a) presenting at least one symbol at at least one first distance in front of at least one eye of a user for stimulating the accommodation of the at least one eye;
b) capturing at least one eye movement of the at least one eye;
c) determining a refraction of the at least one eye with the accommodation of the at least one eye at the at least one first distance;
d) jointly determining the accommodation and the vergence of the at least one eye by:
   determining a change in the refraction of the at least one eye with the accommodation of the at least one eye at the at least one first distance in relation to the accommodation of the at least one eye at at least one second distance;
   determining the vergence of the at least one eye from the at least one eye movement of the at least one eye with the accommodation of the at least one eye at the at least one first distance; and
e) determining a change of myopia of the at least one eye of the user from a ratio of the vergence of the at least one eye to the change in the accommodation from the change in the refraction of the at least one eye with the accommodation of the at least one eye at the at least one first distance in relation to the accommodation of the at least one eye at the at least one second distance,
wherein the jointly determined accommodation and vergence of the at least one eye of the user are used as the values for the control of myopia.

19. An apparatus for data processing, comprising a processor configured to execute a method for jointly determining an accommodation and a vergence, the method comprising the following steps:
a) presenting at least one symbol at at least one first distance in front of at least one eye of a user for stimulating the accommodation of the at least one eye;
b) capturing at least one eye movement of the at least one eye;
c) determining a refraction of the at least one eye with the accommodation of the at least one eye at the at least one first distance;
d) jointly determining the accommodation and the vergence of the at least one eye by
   determining a change in the refraction of the at least one eye with the accommodation of the at least one eye at the at least one first distance in relation to the accommodation of the at least one eye at the at least one second distance;
   determining the vergence of the at least one eye from the at least one eye movement of the at least one eye with the accommodation of the at least one eye at the at least one first distance; and
e) determining a change of myopia of the at least one eye of the user from a ratio of the vergence of the at least one eye to the change in the accommodation from the change in the refraction of the at least one eye with the accommodation of the at least one eye at the at least one first distance in relation to the accommodation of the at least one eye at the at least one second distance.

20. An apparatus for data processing, comprising:
a processor configured to execute a method for determining values for a control of myopia of at least one eye of a user with a method for jointly determining accommodation and vergence of at least one eye of the user, the method comprising the following steps:
a) presenting at least one symbol at at least one first distance in front of at least one eye of a user for stimulating the accommodation of the at least one eye;
b) capturing at least one eye movement of the at least one eye;
c) determining a refraction of the at least one eye with the accommodation of the at least one eye at the at least one first distance;
d) jointly determining the accommodation and the vergence of the at least one eye by:
   determining a change in the refraction of the at least one eye with the accommodation of the at least one eye at the at least one first distance in relation to the accommodation of the at least one eye at at least one second distance;
   determining the vergence of the at least one eye from the at least one eye movement of the at least one eye with the accommodation of the at least one eye at the at least one first distance; and
e) determining a change of myopia of the at least one eye of the user from a ratio of the vergence of the at least one eye to the change in the accommodation from the change in the refraction of the at least one eye with the accommodation of the at least one eye at the at least one first distance in relation to the accommodation of the at least one eye at the at least one second distance,
wherein the jointly determined accommodation and vergence of the at least one eye of the user are used as the values for the control of myopia.

21. A computer-readable non-transitory storage medium comprising instructions that, upon execution by a computer, cause the latter to carry out a method comprising the following steps:
a) presenting at least one symbol at at least one first distance in front of at least one eye of a user for stimulating the accommodation of the at least one eye;
b) capturing at least one eye movement of the at least one eye; and c) determining a refraction of the at least one eye with the accommodation of the at least one eye at the at least one first distance;
d) jointly determining the accommodation and the vergence of the at least one eye by:
   determining a change in the refraction of the at least one eye with the accommodation of the at least one eye at the at least one first distance in relation to the accommodation of the at least one eye at at least one second distance;
   determining the vergence of the at least one eye from the at least one eye movement of the at least one eye with the accommodation of the at least one eye at the at least one first distance; and
e) determining a change of myopia of the at least one eye of the user from a ratio of the vergence of the at least one eye to the change in the accommodation from the change in the refraction of the at least one eye with the accommodation of the at least one eye at the at least one first distance in relation to the accommodation of the at least one eye at the at least one second distance.

22. A computer-readable non-transitory storage medium comprising instructions that, upon execution by a computer, cause the latter to carry out a computer-implemented method for determining values for a control of myopia of at least one eye of a user by a joint determination of accommodation and vergence of at least one eye of the user, the method comprising the following steps:

a) presenting at least one symbol at at least one first distance in front of at least one eye of a user for stimulating the accommodation of the at least one eye;
b) capturing at least one eye movement of the at least one eye; and
c) determining a refraction of the at least one eye with the accommodation of the at least one eye at the at least one first distance;
d) jointly determining the accommodation and the vergence of the at least one eye by:
   determining a change in the refraction of the at least one eye with the accommodation of the at least one eye at the at least one first distance in relation to the accommodation of the at least one eye at at least one second distance;
   determining the vergence of the at least one eye from the at least one eye movement of the at least one eye with the accommodation of the at least one eye at the at least one first distance; and
e) determining a change of myopia of the at least one eye of the user from a ratio of the vergence of the at least one eye to the change in the accommodation from the change in the refraction of the at least one eye with the accommodation of the at least one eye at the at least one first distance in relation to the accommodation of the at least one eye at the at least one second distance,
wherein the jointly determined accommodation and vergence of the at least one eye of the user are used as the values for the control of myopia.

* * * * *